(12) United States Patent
Jankovic et al.

(10) Patent No.: US 9,707,272 B2
(45) Date of Patent: Jul. 18, 2017

(54) METHOD FOR THE TREATMENT OF ACNE BY ADMINISTERING IL-1β ANTIBODY

(75) Inventors: Dragana Jankovic, Basel (CH); Magdalena Kistowska, Dietikon (CH); Emmanuel Contassot, Buschwiller (FR); Lars E. French, Schweiz (CH); Samuel Gehrke, Rapperswil (CH)

(73) Assignee: UNIVERSITAT ZURICH, Zurich (CH)

( * ) Notice: Subject to any disclaimer, the term of this patent is extended or adjusted under 35 U.S.C. 154(b) by 540 days.

(21) Appl. No.: 14/232,272

(22) PCT Filed: Jul. 11, 2012

(86) PCT No.: PCT/EP2012/063617
§ 371 (c)(1),
(2), (4) Date: Mar. 19, 2014

(87) PCT Pub. No.: WO2013/007763
PCT Pub. Date: Jan. 17, 2013

(65) Prior Publication Data
US 2014/0199320 A1    Jul. 17, 2014

(30) Foreign Application Priority Data
Jul. 12, 2011  (EP) ..................... 11173700

(51) Int. Cl.
| | | |
|---|---|---|
| A61K 39/395 | (2006.01) | |
| A61K 38/20 | (2006.01) | |
| A61K 31/64 | (2006.01) | |
| C07K 16/24 | (2006.01) | |
| C07K 16/28 | (2006.01) | |
| A61K 31/50 | (2006.01) | |
| G01N 33/68 | (2006.01) | |
| A61K 39/00 | (2006.01) | |

(52) U.S. Cl.
CPC .......... *A61K 38/2006* (2013.01); *A61K 31/50* (2013.01); *A61K 31/64* (2013.01); *C07K 16/245* (2013.01); *C07K 16/2866* (2013.01); *G01N 33/6869* (2013.01); *A61K 2039/505* (2013.01)

(58) Field of Classification Search
CPC ............ A61K 2039/55533; A61K 2039/55527
See application file for complete search history.

(56) References Cited

PUBLICATIONS

Dinarello et al (2012), Nat. Rev. Drug Discov. 11(8): 633-652.*
Globe Newswire, Feb. 20, 2013.*
M. Brenner et al: "Targeted treatment of pyoderma gangrenosum in PAPA (pyogenic arthritis, pyoderma gangrenosum and acne) syndrome with the recombinant human interleukin-1 receptor antagonist anakinra" British Journal of Dermatology, vol. 161, No. 5, Nov. 1, 2009, pp. 1199-1201.
Grange Philippe A et al: "Production of superoxide anions by keratinocytes initiates P. acnes-induced inflammation of the skin.", PLOS Pathogens, vol. 5, No. 7, Jul. 2009, pp. 1-14.
Hal M. Hoffman et al: "Inflammasome and IL-1[beta]-Mediated Disorders", Current Allergy and Asthma Reports, vol. 10, No. 4, Apr. 28, 2010, pp. 229-235.

* cited by examiner

*Primary Examiner* — Prema Mertz
(74) *Attorney, Agent, or Firm* — JMB Davis Ben-David

(57) ABSTRACT

The invention provides inhibitors capable of binding to a member of the inflammasome group comprised of IL-1β, IL-1 receptor type 1, NLRP3, ASC, Caspase-1 and cathepsin B with a dissociation constant of 10-8 mol/l or smaller for the prevention and treatment of acne, specifically an antibody, an antibody fragment, an antibody-like molecule, an oligopeptide of 6 to 30 amino acid residues, a nucleic acid aptamer molecule of 10 to 75 nucleotides in length or a soluble polypeptide comprising a contiguous amino acid sequence of at least 30 amino acids comprised within the protein sequence of a member of the group comprised of IL-1β, IL-1 receptor type 1, IL-1 receptor type 2, NLRP3, ASC and Caspase-1. Similarly, an interfering RNA or an antisense modulator of gene expression of IL-1β, I L-1β receptor type 1, NLRP3, ASC, Caspase-1 and cathepsin B are provided for the prevention or treatment of acne.

2 Claims, 22 Drawing Sheets

SEQUENCE LISTING

```
<160> NUMBER OF SEQ ID NOS: 3

<210> SEQ ID NO 1
<211> LENGTH: 118
<212> TYPE: PRT
<213> ORGANISM: artificial
<220> FEATURE:
<223> OTHER INFORMATION: antibody fragment

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Asp Leu Arg Thr Gly Pro Phe Asp Tyr Trp Gly Gln Gly Thr
            100                 105                 110

Leu Val Thr Val Ser Ser
        115

<210> SEQ ID NO 2
<211> LENGTH: 107
<212> TYPE: PRT
<213> ORGANISM: artificial
<220> FEATURE:
<223> OTHER INFORMATION: antibody fragment

<400> SEQUENCE: 2

Glu Ile Val Leu Thr Gln Ser Pro Asp Phe Gln Ser Val Thr Pro Lys
1               5                   10                  15
```

-continued

```
Glu Lys Val Thr Ile Thr Cys Arg Ala Ser Gln Ser Ile Gly Ser Ser
         20                  25                  30

Leu His Trp Tyr Gln Gln Lys Pro Asp Gln Ser Pro Lys Leu Leu Ile
         35                  40                  45

Lys Tyr Ala Ser Gln Ser Phe Ser Gly Val Pro Ser Arg Phe Ser Gly
     50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                 85                  90                  95

Thr Phe Gly Pro Gly Thr Lys Val Asp Ile Lys
             100                 105

<210> SEQ ID NO 3
<211> LENGTH: 7
<212> TYPE: PRT
<213> ORGANISM: artificial
<220> FEATURE:
<223> OTHER INFORMATION: all positions D amino acids, terminal amide
      (NH2)

<400> SEQUENCE: 3

Arg Tyr Thr Val Glu Leu Ala
1               5
```

METHOD FOR THE TREATMENT OF ACNE BY ADMINISTERING IL-1β ANTIBODY

CROSS-REFERENCE TO RELATED APPLICATIONS

This is the U.S. National Stage of International Application No. PCT/EP2012/063617, filed Jul. 11, 2012, which was published in English under PCT Article 21(2), which in turn claims the benefit of European Patent Application No. 11173700.3, filed Jul. 12, 2011.

This invention relates to the prevention and treatment of Acne vulgaris (acne). Specifically, modulators of the NLRP3 inflammasome IL-1β pathway, particularly antibodies to, or small molecule inhibitors of, members of the NLRP3 inflammasome IL-1β pathway are provided for the prevention and treatment of acne.

Acne vulgaris is a common skin disease caused by inflammation of the hair follicles and sebaceous glands. One of the factors that contribute to the occurrence of acne is *Propionibacterium acnes* (*P. acnes*), part of the normal skin flora, but which can be significantly increased in patients with acne. The role of *P. acnes* as an etiological factor in acne is well established.

Activation of Toll-Like Receptors (TLR) or NOD-like receptors (NLR) on innate immune cells initiates an immediate immune response involving the production of pro-inflammatory cytokines such as IL-1β. Induction of IL-1β secretion is thought to require two independent events: first, an increase in pro-IL-1β levels through NF-κB-mediated transcriptional activation; and second, activation of caspase-1 that results in processing of pro-IL-1β and the subsequent release of IL-1β. Activation of caspase-1 is controlled by a cytosolic complex of proteins known as the inflammasome. This multiprotein complex is composed of a NLRP (NACHT domain, leucin-rich repeat domain and pyrin domain containing protein) family member, the protein ASC (apoptotic speck protein, containing a caspase recruitment domain), and caspase-1 and/or -5.

The objective of the present invention is to provide safe and efficacious means for the prevention and treatment of acne. This objective is attained by the subject-matter of the independent claims.

The present invention is based on the surprising finding that IL-1β is necessary for an inflammatory response induced by *P. acnes*, and this response must be mediated by NLRP3 inflammasome activation.

According to a first aspect of the invention, an inhibitor capable of binding to a member of the inflammasome group with a dissociation constant of $10^{-8}$ mol/l or smaller is provided for use in a method for the prevention or treatment of acne, wherein the inflammasome group is comprised of IL-1β (Gene ID: 3553), IL-1 receptor type 1 (Gene ID: 3554), NLRP3 (Gene ID: 114548), ASC (Gene ID: 29108), Caspase-1 (Gene ID: 834) and cathepsin B (Gene ID: 1508).

The above and following Gene ID numbers refer to entries of the Gene data base of the United States National Center for Biotechnology Information.

An inhibition of the biological activity of any of the members of the inflammasome group defined in the preceding paragraph results in a significantly reduced concentration of IL-1β at an inflammation site caused by the presence of *P. acnes*. By decreasing the amount of IL-1β, immigration of neutrophil granulocytes is reduced and a pathogenic inflammation reaction of the affected skin is suppressed.

Such an inhibitor according to the first aspect of the invention may be an antibody, an antibody fragment, an antibody-like molecule, an oligopeptide or a nucleic acid aptamer molecule of 10 to 75 nucleotides in length, any of which binds to and thereby inhibits one of IL-1β, IL-1 receptor type 1, NLRP3, ASC, Caspase-1 and cathepsin B and thus decreases or abrogates the biological activity of IL-1β topically or systemically.

Antibodies against a member of the inflammasome group can be generated e.g. by immunization of knockout mice using the virus-like particle system, or by injection of recombinant protein in knockout mice.

An antibody fragment may be a Fab fragment, which is the antigen-binding fragment of an antibody, or a single-chain variable fragment, which is a fusion protein of the variable region of heavy and the light chain of an antibody connected by a peptide linker. An antibody-like molecule may be a repeat protein, such as a designed ankyrin repeat protein (Molecular Partners, Zurich). An antibody fragment or an antibody-like molecule according to the invention is able to decrease the concentration of active IL-1β in the skin by binding one of IL-1β, IL-1 receptor type 1, NLRP3, ASC, Caspase-1 and cathepsin B and thus, inhibit the biological activity of IL-1β.

Suitable inhibitors according to the first aspect of the invention may also be developed by evolutive methods such as phage display, ribosome display or SELEX, wherein polypeptide or oligonucleotides are selected due to their binding affinity to a target of interest. Additionally, the binding affinity of an identified inhibitor may be improved by cycles of evolution of the amino acid sequence or nucleotide sequence, and selection of the evolved inhibitors may be effected based on the required affinity.

An oligopeptide according to a first aspect of the invention may be a peptide derived from the recognition site of the IL-1 receptor that competes with the receptor for IL-1β. Vice versa, an oligopeptide may be derived from the part of IL-1β molecule that is recognized by its receptor and binding of this oligopeptide results in inhibition of the receptor. Binding of such an oligopeptide must not result in an activation of the downstream signal of the receptor.

Alternatively, an inhibitor according to the first aspect of the invention may be a soluble polypeptide, comprising a contiguous amino acid sequence of at least 30 amino acid residues taken from the protein sequence of a member of the group comprised of IL-1β, IL-1 receptor type 1, IL-1 receptor type 2 (Gene ID: 7850), NLRP3, ASC and Caspase-1. The soluble polypeptide is capable to interact with a member of the inflammasome group described above. "Interacting" in the sense of the instant invention means the specific binding of a molecule to another molecule. Such interacting pairs are, for example IL-1β and IL-1 receptor or ASC and Caspase-1. Thus, such soluble polypeptide can be used to inhibit a member of the inflammasome group by binding. Optionally, the soluble polypeptide is linked to an Fc domain of an antibody.

According to a preferred embodiment of the first aspect of the invention, an inhibitor selected from the group comprised of the extracellular domain of IL-1 receptor type 2,
canakinumab (Novartis),
gevokizumab (Xoma),
AMG 108 (Amgen Inc.),
rilonacept (Regeneron Pharmaceuticals),
anakinra (Biogen),
GSK1827771 (GlaxoSmithKline),
LY21899102 (Eli Lilly) and
VRS-826 (Versatis, Inc.)

is provided for the prevention or treatment of acne.

The IL-1 receptor type 2 is a receptor that binds IL-1β without activating downstream signals and acts as a decoy receptor.

Canakinumab (CAS registration number: 914613-48-2) is a human monoclonal anti-IL-1β immunoglobulin, comprising a heavy chain and a light chain, wherein the heavy chain of the immunoglobulin comprises the sequence shown in Seq. Id. No.1 and the light chain of the immunoglobulin comprises the sequence shown in Seq. Id. No. 2.

```
Canakinumab heavy chain variable region:
                                    Seq. Id. No. 1
QVQLVESGGGVVQPGRSLRLSCAASGFTFSVYGMNWVRQAPGKGLE

WVAIIWYDGDNQYYADSVKGRFTISRDNSKNTLYLQMNGLRAEDTA

VYYCARDLRTGPFDYWGQGTLVTVSS.,

Canakinumab light chain variable region:
                                    Seq. Id. No. 2
EIVLTQSPDFQSVTPKEKVTITCRASQSIGSSLHWYQQKPDQSPKL

LIKYASQSFSGVPSRFSGSGSGTDFTLTINSLEAEDAAAYYCHQSS

SLPFTFGPGTKVDIK.,
```

Gevokizumab (CAS registration number: 1129435-60-4), also termed XOMA-052, is an immunoglobulin $G_2$ humanized monoclonal antibody against human IL-1β.

AMG 108 (Amgen Inc.) is a fully human immunoglobulin $G_2$ antibody that specifically binds IL-1 receptor type 1 and inhibits the biological activity of IL-1β.

Rilonacept is a dimeric fusion protein consisting of the ligand binding domain of the IL-1 receptor and the IL-1 receptor accessory protein bound to the Fc domain of a human immunoglobulin $G_1$.

GSK182771 is a domain-targeting antibody directed against the IL-1 receptor.

Anakinra (CAS registration number 143090-92-0) is an interleukin-1 receptor antagonist protein that competes with IL-1β for its receptor.

According to a second aspect of the invention, a modulator of gene expression of a member of the inflammasome group is provided for the prevention or treatment of acne wherein the inflammasome group is comprised of IL-1β, IL-1 receptor type 1, NLRP3, ASC, Caspase-1 and cathepsin B.

A modulator according to the second aspect of the invention may be a single-stranded or double-stranded interfering ribonucleic acid oligomer or a precursor thereof, comprising a sequence tract complementary to an mRNA molecule encoding a member of the inflammasome group described above.

The art of silencing or "knocking down" genes, by degradation of mRNA or other effects, is well known. Examples of technologies developed for this purpose are siRNA, miRNA, shRNA, shmiRNA, or dsRNA. A comprehensive overview of this field can be found in Perrimon et al, Cold Spring Harbour Perspectives in Biology, 2010, 2, a003640.

Alternatively, a modulator according to the second aspect of the invention may be a single-stranded or double-stranded antisense ribonucleic or deoxyribonucleic acid, comprising sequences complementary to a sequence comprised in an operon expressing a gene of a member of the inflammasome group. Such operon sequence may include, without being restricted to, an intron, an exon, an operator, a ribosome binding site or an enhancer sequence. Such antisense molecules may be 12-50 nucleotides in length.

According to a third alternative of the second aspect of the invention, the modulator may be an expression vector, comprising a sequence encoding an interfering ribonucleic acid oligomer or precursor thereof, as is described in the preceding paragraph. Optionally, the sequence is under control of an RNA-polymerase promoter sequence operable in a mammalian cell. Such expression vector allow for the production of an interfering RNA within the cell. Methods for making and using such expression vectors are known in the art.

According to another aspect of the invention, a compound for use in a method for the prevention or treatment is provided, wherein the compound is selected from the group comprised of D-Arg-D-Tyr-D-Thr-D-Val-D-Glu-D-Leu-D-Ala-$NH_2$
(AGP-101.10; SEQ ID 003);

2-Benzyl-5-(4-chlorophenyl)-6-[4-(methylthio)phenyl]-2H-pyridazin-3-one (K-832):

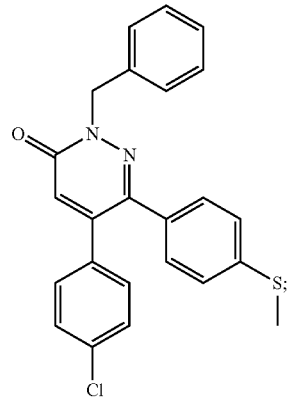 [SMILES: CSc1ccc(-c2nn(Cc3ccccc3)c(=O)cc2-c2ccc(Cl)cc2)cc1]

3-Phenyl-4,5-dihydro-5-isoxasole acetic acid (VGX-1027):

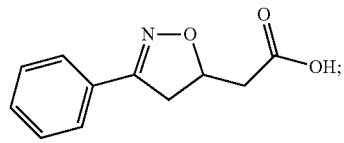 [SMILES: O=C(O)CC1CC(c2ccccc2)=NO1]

4,5-Diacetoxy-9,10-dioxo-anthracene-2-carboxylic acid (diacerin):

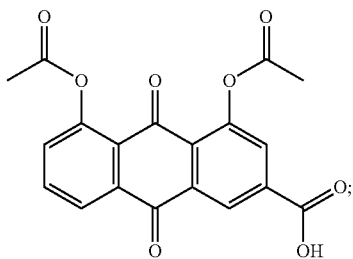 [SMILES: CC(=O)Oc1cccc2c1C(=O)c1c(OC(C)=O)cc(C(=O)O)cc1C2=O]

N-Benzylcarboxy-Val-Ala-Asp-fluormethylketone (Z-VAD-FMK):

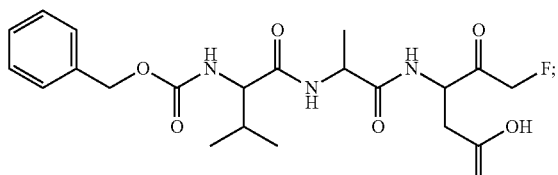

5-Chloro-N-[2-[4-(cyclohexylcarbamoylsulfamoyl)phenyl]ethyl]-2-methoxy-benzamide (Glibenclamide):

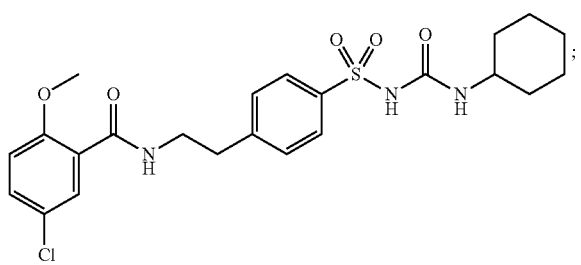 [SMILES: COc1ccc(Cl)cc1C(=O)NCCc1ccc(S(=O)(=O)NC(=O)NC2CCCCC2)cc1]

Dibenziodolium (DPI):

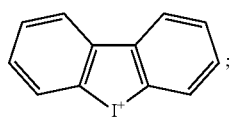

Pyrrolidine dithiocarbamate (PDTC):

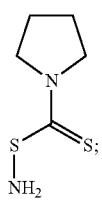

Cytochalasin D:

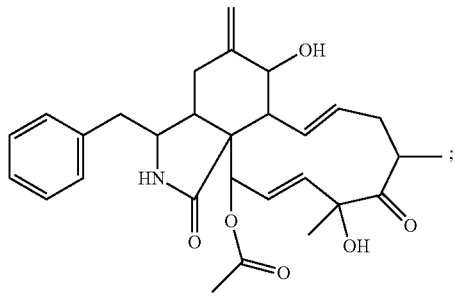 [SMILES: C=C1CC2C(Cc3ccccc3)NC(=O)C23C(OC(C)=O)/C=C/C(C)(O)C(=O)C(C)C/C=C/C3C1O]

N-[3-(Propylcarbamoyl)-oxirane-2-carbonyl]-isoleucyl-proline methyl ester:

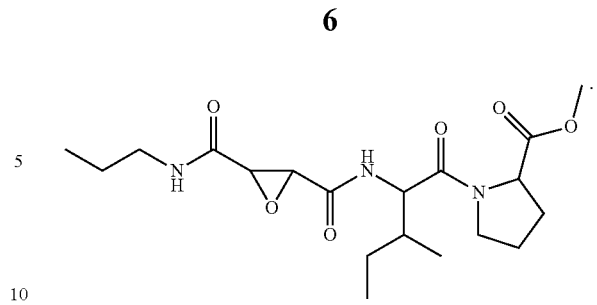

According to yet another aspect of the invention, CYT-103-IL1bQb is provided. CYT-103-IL1bQb is a therapeutic vaccine and consists of modified IL-1β molecules coupled to the virus-like particle Qb. The vaccine induces an immunological response of the host immune system resulting in the formation of anti-IL1β-antibodies and inactivation of IL-1β.

According to another aspect of the invention, a pharmaceutical composition is provided for use in a method for the prevention or treatment of acne, comprising an inhibitor, a modulator or a compound according to the above aspects of the invention.

Pharmaceutical compositions for enteral administration, such as nasal, buccal, rectal or oral administration or, especially, for parenteral administration, such as subcutaneous, intravenous, intrahepatic or intramuscular administration, are preferred. The pharmaceutical compositions comprise from approximately 1% to approximately 95% active ingredient, preferably from approximately 20% to approximately 90% active ingredient.

Similarly, a dosage form for use in a method for the prevention or treatment of acne is provided, comprising an inhibitor, a modulator or a compound according to the above aspects of the invention. Optionally, a pharmaceutical carrier or excipient may be present.

An inhibitor, a modulator or a compound according to the above aspects of the invention can be applied to a subject in any form suitable to the intended treatment. Such a form may be an oral formulation, nasal inhalant, injection, a suppository or a topical formulation. A topical formulation, particularly an ointment or dermal patch, or an injectable formulation is preferred.

For parenteral administration preference is given to the use of solutions of an inhibitor, a modulator or a compound according the above aspects of the invention. Also considered are suspensions or dispersions. Especially preferred are isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal/intraperitoneal and intravenous applications are also considered, for example using a transdermal patch, which allows administration over an extended period of time, e.g. from one to twenty days.

Intravenous or subcutaneous applications are particularly preferred.

An inhibitor, a modulator or a compound according to the above aspects of the invention can be administered alone or in combination with one or more other therapeutic agents. Possible combination therapies can take the form of fixed combinations of the inhibitor, modulator or compound and one or more other therapeutic agents known in the prevention or treatment of acne. The administration can be staggered or the combined agents can be given independently of one another, or in the form of a fixed combination.

According to yet another aspect of the invention, a method for the prevention of treatment of acne is provided, comprising the administration of an inhibitor, a modulator or a compound according to the above aspects of the invention to a patient in need thereof.

The treatment may be for prophylactic or therapeutic purposes. For the administration, the inhibitor, modulator or compound is preferably in the form of a pharmaceutical preparation comprising the inhibitor, modulator, or compound in chemically pure form and optionally, a pharmaceutically acceptable carrier or adjuvants. The inhibitor, modulator or compound is used in an amount effective against acne. The dosage of the active ingredient depends upon the species, its age, weight, and individual condition, the individual pharmacokinetic data, the mode of administration, and whether the administration is for prophylactic or therapeutic purposes. In the case of an individual having a bodyweight of about 70 kg the daily dose administered is from approximately with 0.1 mg/kg to approximately 1000 mg, preferably from approximately 0.5 mg to approximately 100 mg/kg, of an inhibitor, a modulator or a compound according to the above aspects of the invention.

Also within scope of the invention is a method for the manufacture of a medicament for use in a method for the prevention or treatment of acne, comprising the use of an inhibitor, a modulator or a compound according to the above aspects of the invention.

Medicaments according to the invention are manufactured by methods known in the art, especially by conventional mixing, coating, granulating, dissolving or lyophilizing.

According to another aspect of the invention, a method for identifying compounds for the prevention or treatment of acne is provided, comprising the steps:
  incubating myeloid cells in the presence of P. acnes and in the presence of a compound that is to be examined with regard to its suitability as an acne drug;
  measuring the release of secreted IL-1β;
  comparing the response in presence of said compound to a standard response.

Suitable cell for the method are able to synthesize and secrete IL-1β mediated by the NLRP3-inflammasome after exposure to P. acnes. According to a preferred aspect of the above aspect, the method may be a cell-based bioassay, wherein THP-1 cells are incubated in culture medium in the presence of P. acnes. P. acnes stimulates the release of IL-1β into the medium. This release may be measured in absence and presence of a candidate compound for the prevention or treatment of acne. Successful candidate compounds will reduce the IL-1β release.

DETAILED DESCRIPTION OF THE INVENTION

Figure 1:
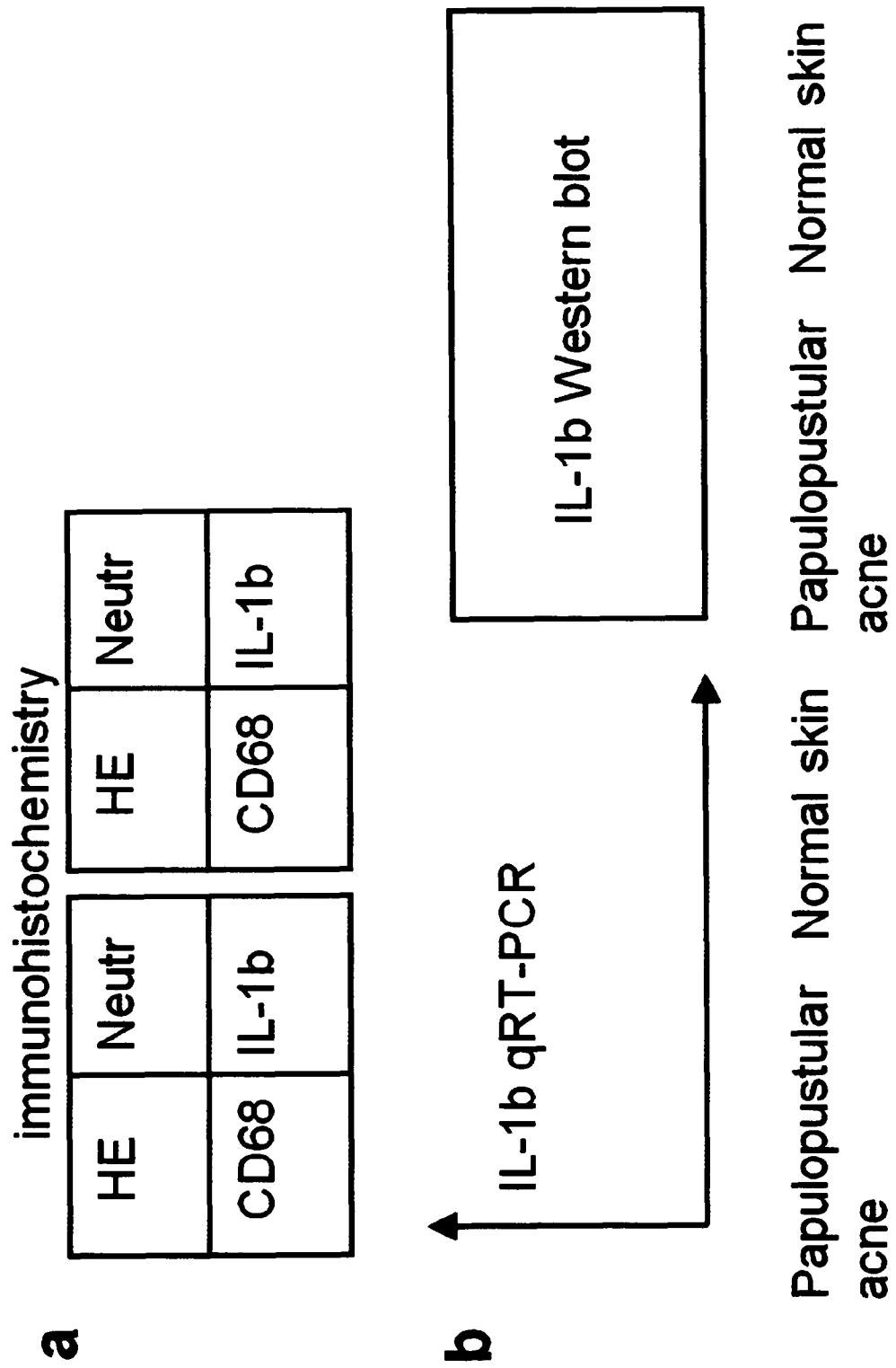
FIG. 1 shows the induction of cytokine secretion of infected monocytes by P. acnes.
Figure 1:
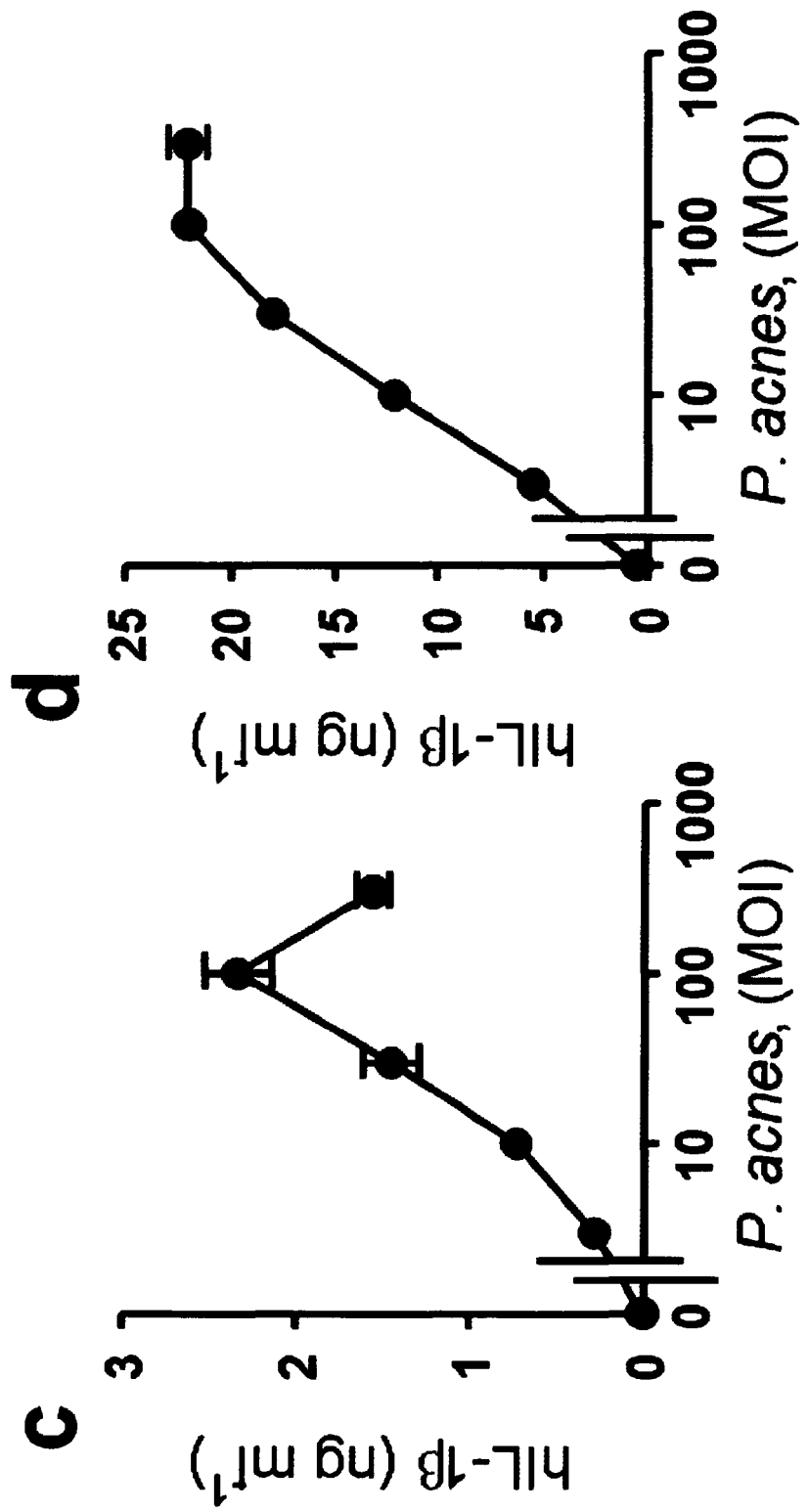
Figure 1:
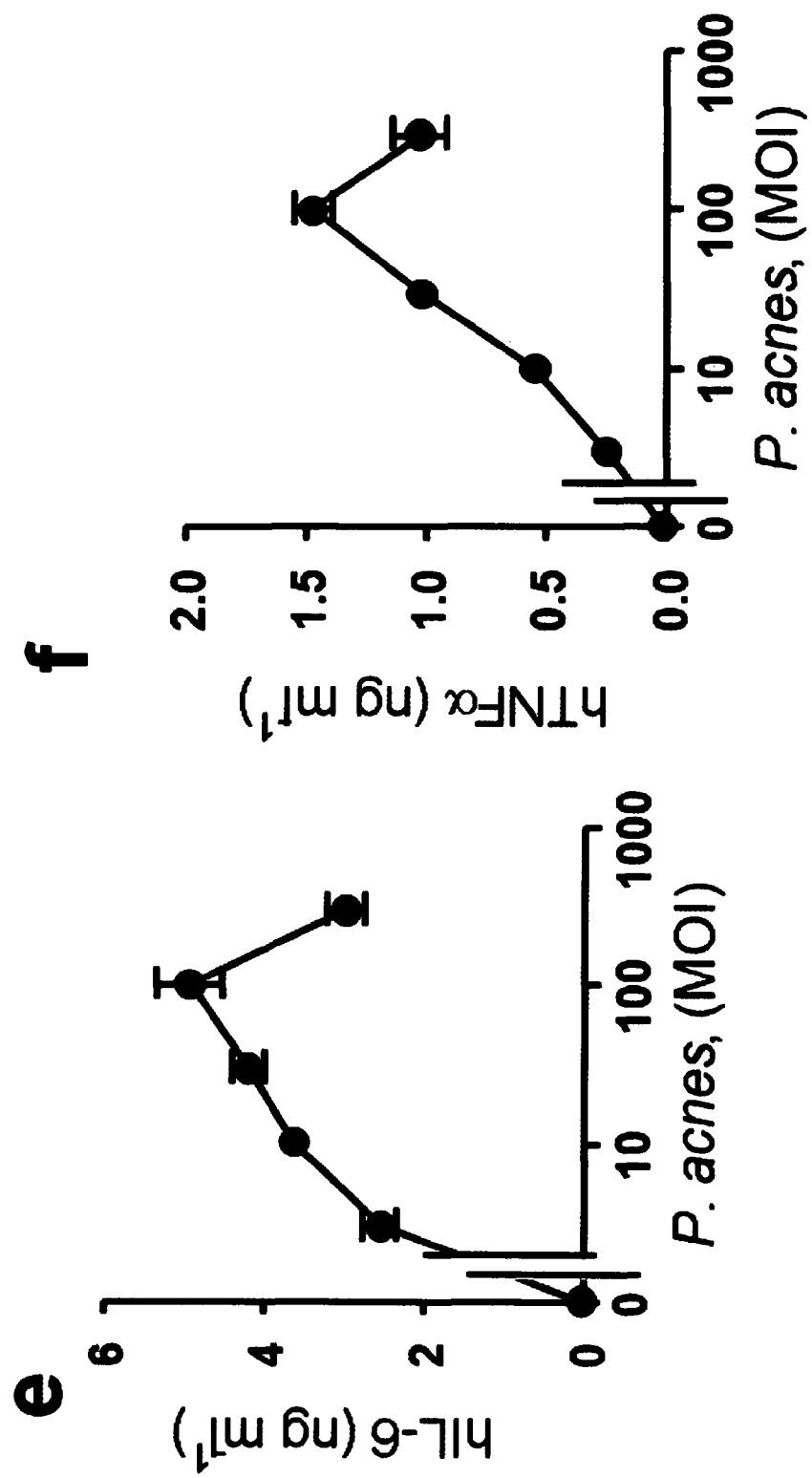
Figure 1:
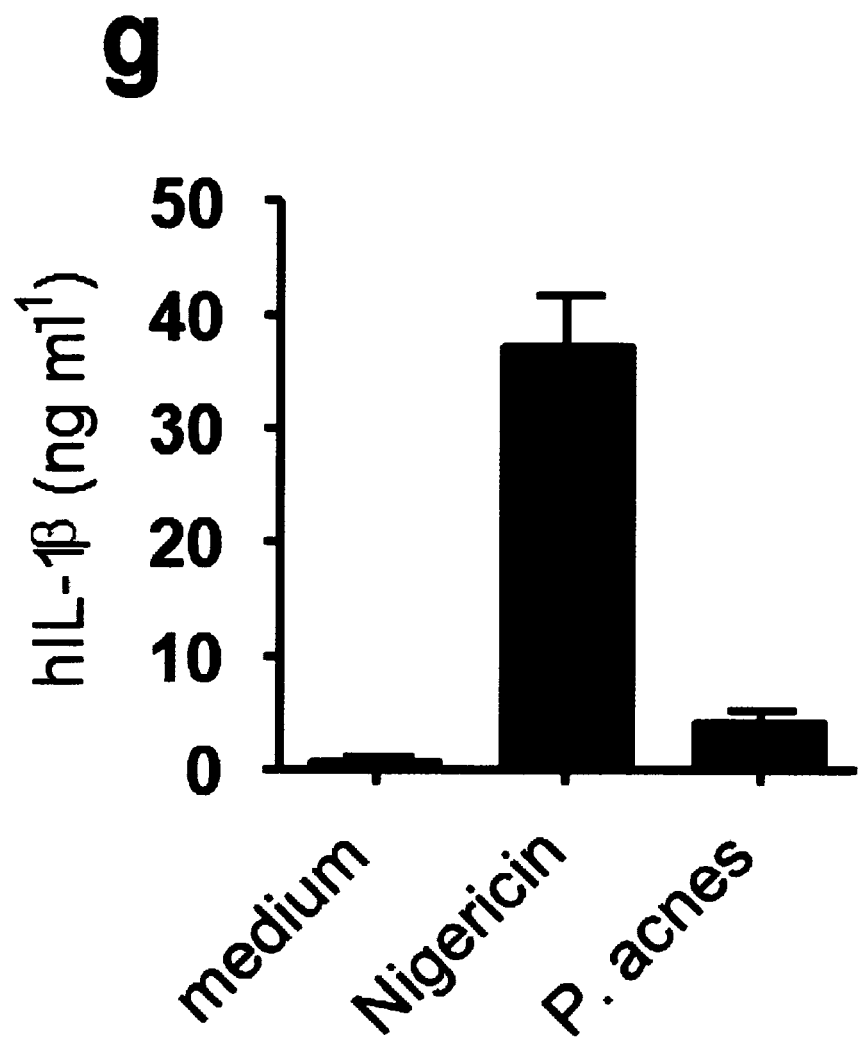

The present invention relates to a method of preventing and treating acne, comprising administering active agents (inhibitors, modulators and compounds as specified in the instant invention) interfering in the NLRP3 inflammasome IL-1β pathway, and the use of such active agents in the prevention or treatment of acne and in the manufacture of medicaments for preventing and treating acne.

The invention further relates to a method of screening for a compound effective in the prevention and treatment of acne, comprising contacting a candidate compound with members of the NLRP3 inflammasome IL-1β pathway and choosing candidate compounds which selectively reduce activity of such member of the NLRP3 inflammasome IL-1β pathway. The invention further relates to compounds selected by these methods of screening.

The action of the members of the NLRP3 inflammasome IL-1β pathway can be modulated by administration of antibodies or antibody fragments directed against IL-1β, IL-1R, or NLRP3, of fusion proteins consisting of IL-1R extracellular domains and the Fc portion of antibodies, of molecules that affect the protein or mRNA expression of IL-1β, IL-1R, or NLRP3 (sRNA; miRNA), as well as of small molecules that interfere with the binding of ligands to the IL-1R. The production of IL-1β, IL-1R, or NLRP3 can be modulated by using siRNA in vitro but also by directly suppressing the promoter activity of genes of IL-1β, IL-1R, or NLRP3 with small molecules or suppressors of the transcription factors involved in the transcription of the respective genes. The action of IL-1β can be inhibited by IL-1 receptor modulators. Additionally, targeting of the NLRP3 inflammasome IL-1β pathway can be achieved by the administration of neutralizing antibodies or antibody fragments to IL-1β, IL-1R, or NLRP3 or by proteins, protein analogues or small synthetic compounds which bind IL-1β and thereby prevent its binding to the IL-1 receptor, or bind to the IL-1 receptor. A further way to prevent binding to the IL-1 receptor is to use soluble IL-1 receptor or fragments thereof.

Antibodies against IL-1β, IL-1R, or NLRP3 can be generated e.g. by immunization of knockout mice by using the virus like particle system, or by injection of recombinant protein in knockout mice.

Examples of NLRP3 inflammasome IL-1β pathway modulators according to the invention are disclosed in the following.

Preferred modulators of the NLRP3 inflammasome IL-1β pathway according to the invention are:

antibodies that bind to IL-1β or NLRP3, antigen binding fragments of an antibody (e.g. Fab fragments) or antibody-like molecules (e.g. repeat proteins) which by binding to IL-1β, or NLRP3 deplete IL-1β or NLRP3 from the extracellular space or that block the binding between IL-1β and its receptors. Antibodies against IL-1β are state of the art and include the well characterized antibodies canakinumab (Novartis) and XOMA052 (Xoma).

antibodies, antigen binding fragments of an antibody (e.g. Fab fragments) or antibody-like molecules (e.g. repeat proteins) which by binding to IL-1R block the action of IL-1β. Such antibodies preferably bind to IL-1R in the region where IL-1β would normally bind, but without inducing IL-1β-signalling. Antibodies against IL-1R are state of the art and include the well characterized antibody AMG 108 (Amgen) described in WO 2004/022718;

fusion proteins consisting of IL-1R extracellular domains and the Fc portion of antibodies, an example of such a protein being rilonacept (Regeneron Pharmaceuticals);

Virus-like particles loaded with IL-1β, IL-1R, or NLRP3 and therefore induce an antibody response directed against these molecules with the effect to block their biological activity;

antisense molecules for downregulation of IL-1β, IL-1R, or NLRP3. These antisense molecules are 12-50 nucleotides in length and encode a given sequence found in the exons or introns of IL-1β, IL-1R, or NLRP3. Moreover, antisense molecules containing a sequence of the IL-1β, IL-1R, or NLRP3 promoters and binding within the promoter region may be used. Finally, antisense molecules binding in the 3' UTR-non translated regions of IL-1β, IL-1R, or NLRP3 are contemplated;

small molecules that inhibit IL-1β, IL-1R, or NLRP3. Small molecules contemplated are synthetic compounds up to a molecular weight of 1000 which have suitable physiological activity and pharmacological properties making them useful for the application as medicaments. Such small synthetic molecules are, for example, found by the screening method of the present invention described below. Alternatively, such small molecules are designed by molecular modelling taking into account possible binding sites of IL-1β, IL-1R, or NLRP3;

proteins and protein analogs which bind IL-1β, IL-1R, or NLRP3, for example, synthetic proteins or protein analogs which mimic the variable region scFv of binding and/or neutralizing antibodies, or antibodies that mimic a binding pocket for IL-1β of the IL-1R. An example of such a protein is anakinra (Biogen).

Most preferred modulators according to the invention are:
canakinumab (Novartis), a human anti-(human interleukin 1(3) immunoglobulin G1 (WO 02/16436);
XOMA052 (Xoma), a human engineered IgG2 antibody (WO 2007/002261);
AMG108 (Amgen), a fully human monoclonal antibody that targets inhibition of the action of interleukin-1 (WO 2004/022718);
GSK1827771, a domain antibody targeting the IL-1 receptor;
LY2189102 (Eli Lilly), a human interleukin 1 monoclonal antibody;
rilonacept (Regeneron Pharmaceuticals), a fusion protein consisting of human cytokine receptor extracellular domains and the Fc portion of human IgG;
anakinra (Biogen), a recombinant form of naturally-occurring IL-1 receptor antagonist;
diacerein (4,5-diacetyloxy-9,10-dioxoanthracene-2-carboxylic acid), from e.g. Abiogen Pharma;
VRS826 (Versartis, Inc.), an interleukin-1 receptor antagonist (IL1ra-rPEG);
APG10110 (Allostera Pharma), an allosteramer which is an oral IL-1R inhibitor;
K832 (Kowa Company), a cytokine production inhibitor;
VGX-1027 (Inovio Biomedical Corporation), an interleukin-1 inhibitor.

Another aspect of the invention relates to the use modulators of the NLRP3 inflammasome IL-1β pathway as described hereinbefore in the prevention and treatment of acne, and in the manufacture of medicaments for treating these diseases.

The invention further relates to a method of screening for a compound effective in the prevention and treatment of acne comprising contacting a candidate compound with a member of the NLRP3 inflammasome IL-1β pathway and choosing candidate compounds which selectively reduce the activity of such member of the NLRP3 inflammasome IL-1β pathway.

Modulators of the NLRP3 inflammasome IL-1β pathway activity are identified by contacting a member of the NLRP3 inflammasome IL-1β pathway with a candidate compound. A control assay with the corresponding member of the NLRP3 inflammasome IL-1β pathway in the absence of the candidate compound is run in parallel. A decrease in activity in the presence of the candidate compound compared to the level in the absence of the compound indicates that the candidate compound is a NLRP3 inflammasome IL-1β pathway modulator.

Concepts and Evidence Behind the Invention

It was shown that *P. acnes* is a strong trigger of IL-1β production in the skin in vivo. Exposure of monocytes to *P. acnes* led to NLRP3-inflammasome activation, caspase-1 cleavage and processing of the mature form of IL-1β in a manner dependent on phagocytosis, subsequent lysosomal destabilization, ROS production, and cellular $K^+$ efflux. Consistent with this, in mice *P. acnes* induces neutrophilic skin lesions reminiscent of acne in a NLRP3-inflammasome-, IL-1β-dependent-, and TLR-2-independent manner that requires the presence of antigen presenting cells of myeloid origin.

The central role of IL-1β in mediating *P. acnes*-induced cutaneous inflammation was further verified by selective blockade of neutrophilic skin infiltration in vivo upon administration of monoclonal anti-IL1β antibody and an IL-1 receptor antagonist. These findings indicate that sensing of *P. acnes* in the skin by the NLRP3 inflammasome can trigger IL-1β-dependent, TLR-2 independent neutrophilic skin inflammation, and identifies IL-1β and NLRP3 as a novel targets for the therapy of inflammatory acne vulgaris.

EXAMPLES

Example 1

P. acnes Induces Cytokine Secretion from Infected Monocytes

For Western blotting cell culture supernatants were precipitated by addition of 0.25 volumes of trichloroacetic acid (100% w/v), 10 min incubation on ice and centrifugation for 5 min at 14,000 g. Protein pellet was washed twice with ice-cold acetone, centrifuged as described above and dried at 70° C. Cells were lysed with buffer (10 mM Tris pH 7.5, 1% NP-40, 150 mM NaCl, 5 mM EDTA,) containing a protease inhibitor cocktail. Proteins were separated on a NuPAGE gel in accordance with the manufacturer's protocol and transferred to a Hybond-C-Extra membrane by electroblotting. The membranes were blocked with 5% gelatin in 1×PBS and 0.5% Tween-20 and then probed with primary antibodies as follows: rabbit polyclonal anti-human mature (17 kDa) IL-1β (D116), rabbit polyclonal anti-human IL-1β, goat polyclonal anti-mouse IL-1b, rabbit polyclonal anti-ASC (AL117), rabbit polyclonal anti-human caspase-1 (sc622), mouse IgG2b anti-NLRP3 (Cryo-2), rabbit polyclonal anti-b-actin. Appropriate HRP-conjugated secondary antibodies were used and proteins were detected using ECL reagent.

P. acnes (DSM 1897) was cultured in anaerobic conditions on cooked meat medium supplemented with yeast extract (5 g/l), $K_2HPO_2$ (5 g/l), resaurin (1 mg/l), and cystein chloride (0.5 g/l) at 37° C. Bacteria were harvested by centrifugation at 5,000 at 10 min, washed and suspended in PBS or medium for experiments.

Monocytes from healthy donors were obtained from peripheral blood mononuclear cells (PBMC). PBMC were purified from buffy-coat using a density gradient (Ficoll-Paque). Monocytes were sorted from PBMC using anti-CD14-labeled magnetic beads.

Freshly isolated human monocytes were stimulated with indicated multiplicity of infection (MOI) of live P. acnes for 24 h (FIG. 1c-f). Secreted IL-1β from P. acnes-infected monocytes (FIG. 1c) or upLPS (ultra pure lipopolysaccharide) primed and P. acnes-infected monocytes (FIG. 1d) was determined by ELISA. IL-6 (FIG. 1e) and TNFα (FIG. 1f) release from P. acnes-exposed cells was determined by ELISA. Primary keratinocytes were exposed to P. acnes or to nigericin during 24 h and IL-1β secretion was measured by ELISA (FIG. 1g). Results represent the mean values and standard deviation (s.d.). Data are representative of experiments done three times.

Within 24 h of exposure to P. acnes, significant secretion of IL-6, TNFα and IL-1β could be detected in culture supernatants as assessed by ELISA, and IL-1β levels in the supernatant further increased when myeloid cells were pre-stimulated with upLPS or PMA (phorbol-12-myristate-13-acetate).

Example 2

P. acnes Activates Caspase-1- and ASC-Dependent NLRP3 Inflammasome

Human THP1 promonocytic leukemia cells were grown in RPMI 1640 medium, supplemented with 10% FCS, 1% Antibiotic-Antimycotic, 1 mM sodium-pyruvate, 2 mM GlutaMAX solution.

Mouse bone-marrow-derived dendritic cells (BMDC) were obtained by differentiation of bone marrow cells from 6-10 weeks old mice for 8 days in RPMI 1640 medium supplemented like above and in the presence of 20% X-63 cells (mGM-CSF-producing cells) supernatant.

For infection experiments THP1 cell were differentiated for 3 h with 500 nM phorbol-12-myristate-13-acetate (PMA), washed and platted one day before stimulation. Human monocytes and mouse BMDC were primed overnight with ultra-pure LPS (E. coli 0111:B4, 100 ng/ml) in antibiotic-free medium. Twelve hours later, medium was replaced and cells were infected with live or heat inactivated P. acnes at the indicated multiplicity of infection (MOI) or stimulated with MSU (mono sodium urate, 150 mg/ml), nigericin (20 mM), silica (500 mg/ml), Zymosan A (200 mg/ml) for indicated time. ATP (5 mM) that was added to the cells 30 min prior to collection of supernatants.

mRNA were isolated from THP1 cells using the Qiagen RNeasy kit following manufacturers instructions, and total RNA was converted into cDNA by standard reverse transcription with Superscript III reverse transcriptase. Quantitative PCR was performed using Power SYBR Green PCR Master Mix. The primer sequences were obtained from http://pqa.mgh.harvard.edu/primerbank/: for human GAPDH: forward 5'-ATGGGGAAGGTGAAGGTC-3', reverse 5'GGGGTCATTGATGGCAACAATA-3' reverse; for human NLRP1: forward 5'-ATTCCAGTTTGTGC-GAATCCA-3', reverse 5'-GTTCCTTGGGGAGTATTTC-CAG-3'. The real-time PCR included an initial denaturation at 95° C. for 10 min, followed by 40 cycle of 95° C. for 30 s, 55° C. for 1 min, 72° C. for 1 min, and one cycle of 95° C. for 1 min, 55° C. for 30 s, 95° C. for 30 s.

THP1 cells stably expressing shRNA against lamin NC, ASC, caspase-1, NLRP1 and NLRP3 were obtained by transducing THP1 cells with lentiviral particles. Briefly gene specific shRNA were generated by inserting oligonucleotides targeting lamin NC, ASC, caspase-1, NLRP3 or NLRP1 into pSUPER vector and subsequent cloning into lentiviral vector pAB286.1. Second-generation packaging plasmids pMD2-VSVG and pCMV-R8.91 were used for lentivirus production and infection.

Figure 2:
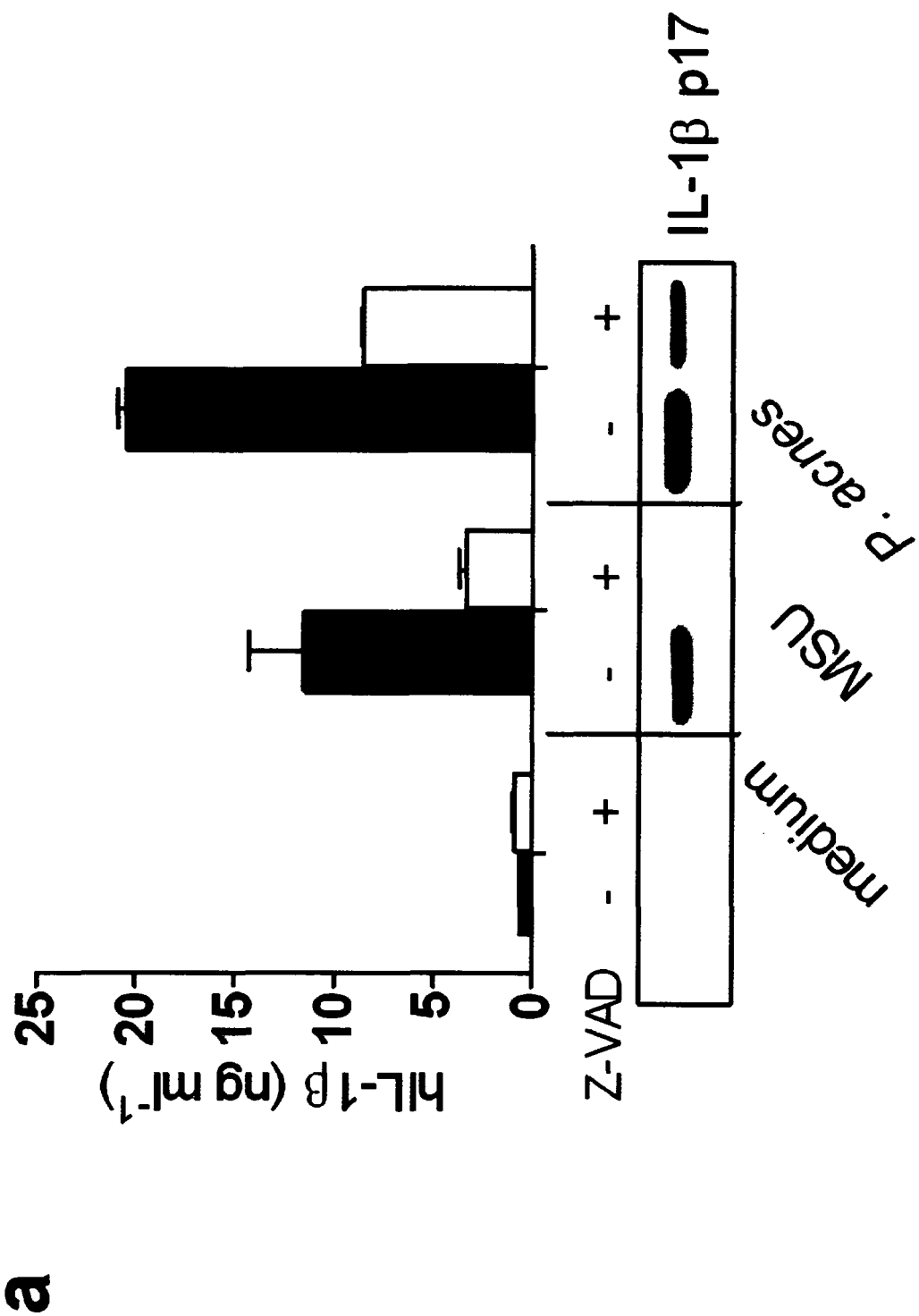
FIG. 2 shows the activation of NLRP3-inflammasome by P. acnes.
Figure 2:
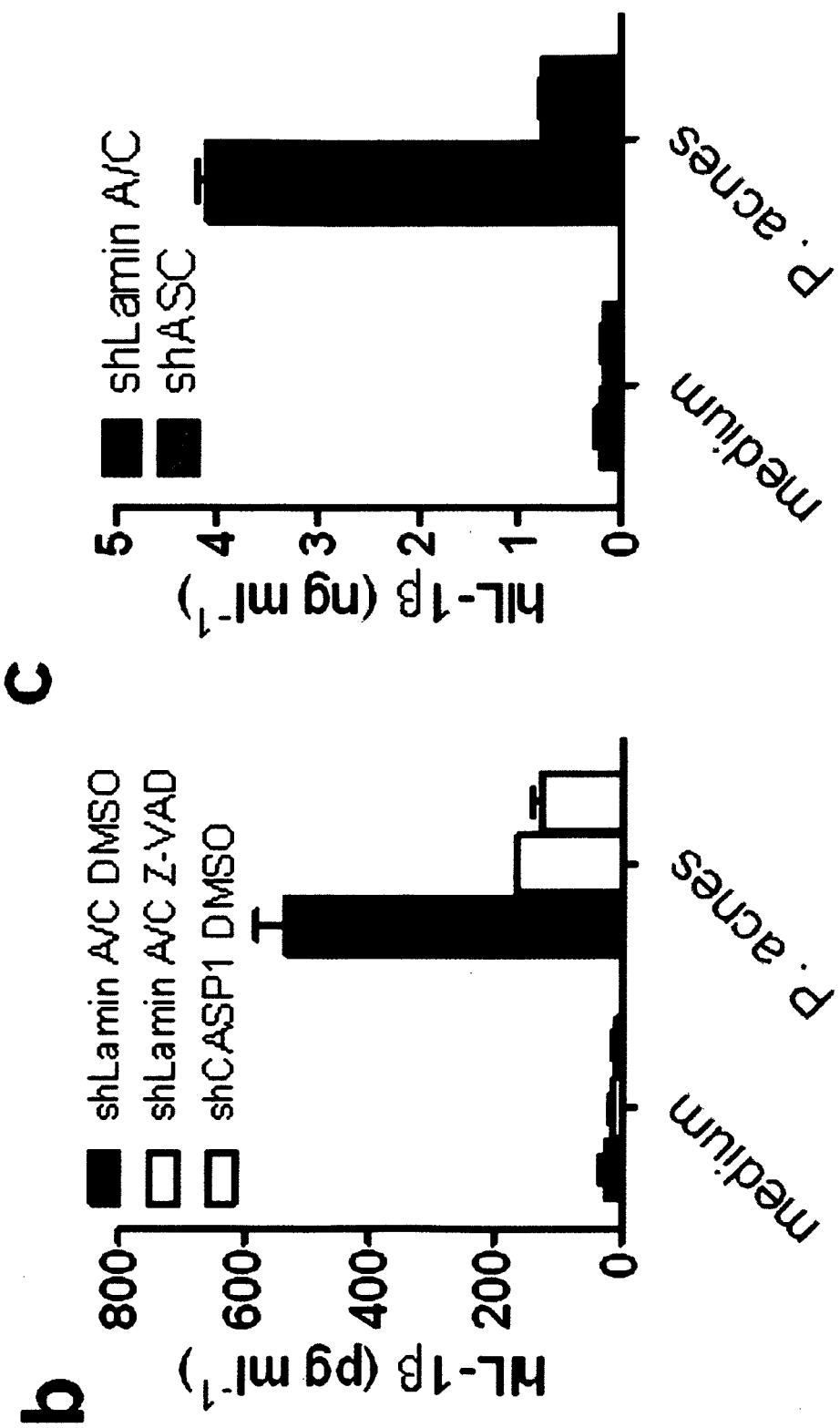
Figure 2:
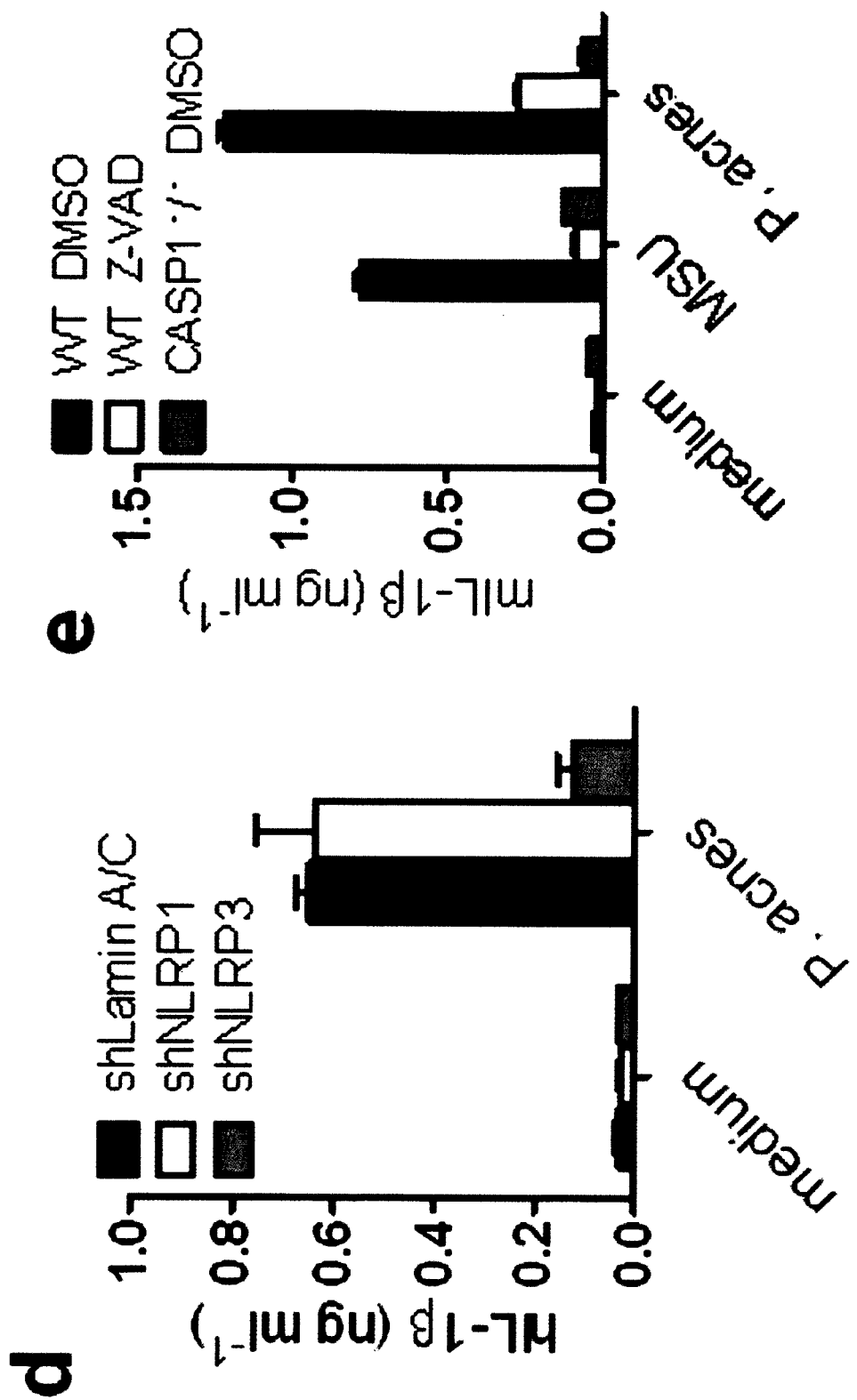
Figure 2:
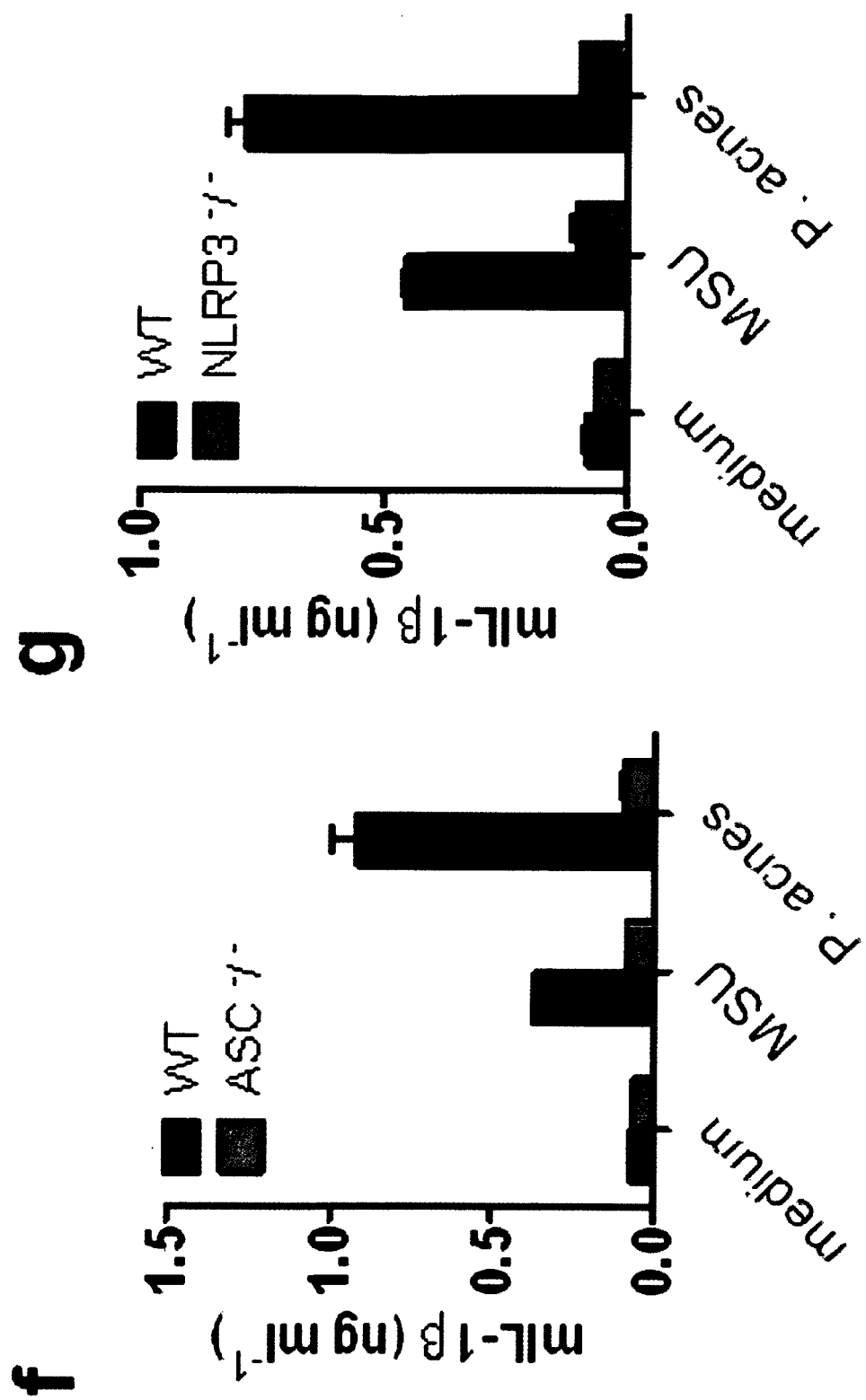
Figure 2:
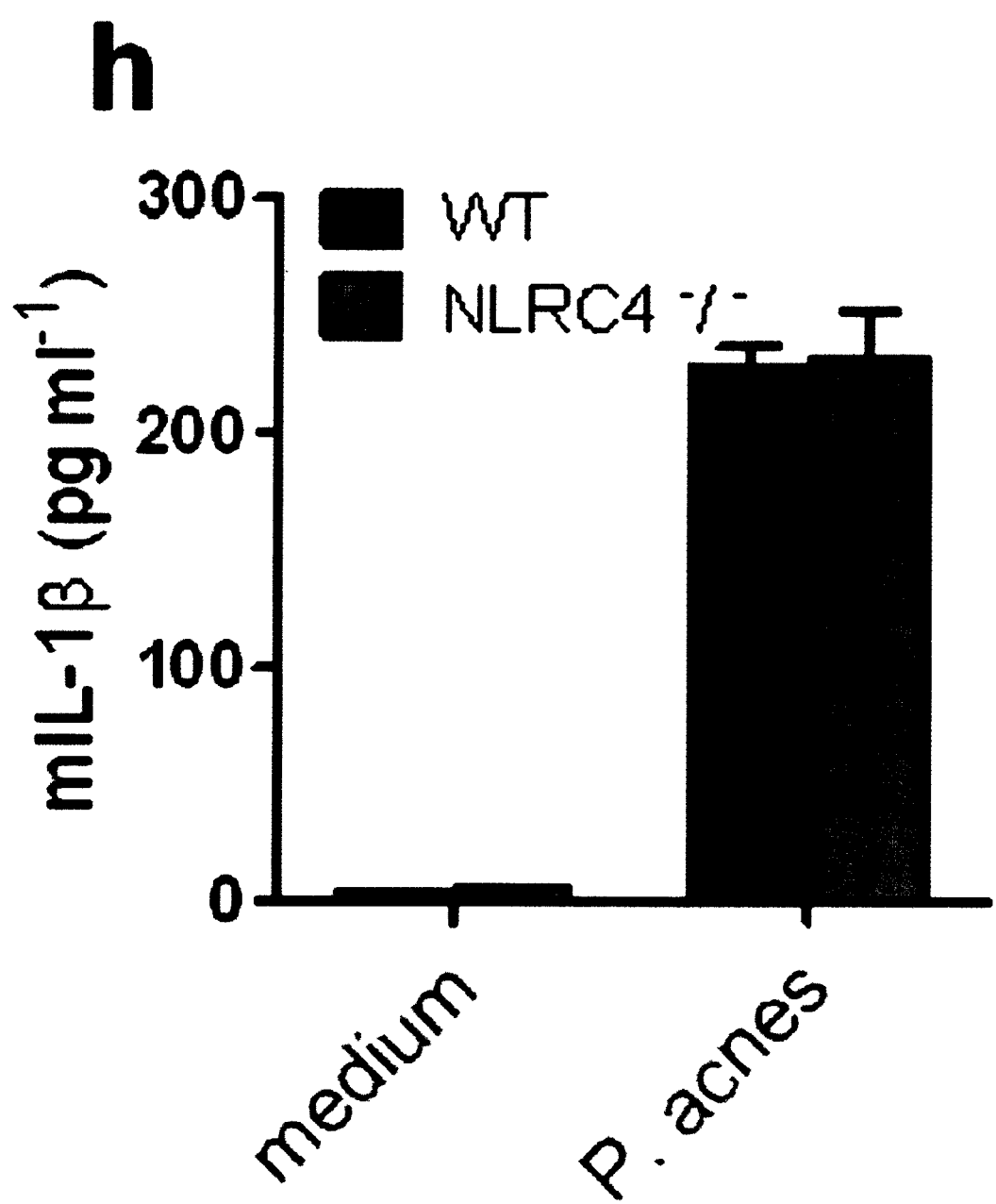

Human monocytes were primed with upLPS and infected with P. acnes (MOI=100) or stimulated with MSU crystals (150 mg/ml) in the presence of vehicle (DMSO) or pan-caspase inhibitor (Z-VAD-fmk, 10 mM) for 24 h (FIG. 2a). IL-1β secretion was determined by ELISA and mature IL-1β release (IL-1β p17) by western blot. Data are representative of two experiments. FIG. 2b-d shows ELISAs of secreted IL-1β from THP-1 transfected with shRNA to Caspase-1 (shCASP1) (FIG. 2b), ASC (shASC) (FIG. 2c), NLRP1 (shNLRP1) or NLRP3 (shNLRP3) (FIG. 2d). Lamin shRNA was used as irrelevant control. FIG. 2e-h show ELISAs of secreted IL-1β from WT, Caspase-1$^{-/-}$ (CASP1) (FIG. 2e), ASC$^{-/-}$ (FIG. 2f), NLRP3$^{-/-}$ (FIG. 2g), NLRC4$^{-/-}$ (FIG. 2h) murine bone-marrow-derived dendritic cells (BMDC) pulsed with upLPS and stimulated with P. acnes (MOI=300) or MSU crystals (150 mg/ml) in the presence of vehicle (DMSO) or Z-VAD-fmk (10 mM) when indicated. Mean and s.d are presented. All results are representative of experiments repeated three times.

In P. acnes—as in MSU-exposed (positive control) human monocytes, the processing and secretion of IL-1β was strongly inhibited in the presence of the pan-caspase inhibitor Z-VAD (FIG. 2a). Moreover and in spite of normal pro-IL1β levels, THP1 cells transfected with caspase-1-shRNA (FIG. 2b) as well as BMDC from caspase-1 deficient mice (FIG. 2e) were unable to process or secrete IL-1β either upon P. acnes exposure or stimulation with the well-known inflammasome activators MSU and nigericin.

THP1 cells transduced with shRNA to ASC (FIG. 2c) or NLRP3 (FIG. 2d) exhibited a strongly reduced IL-1β secretion upon P. acnes exposure when compared to THP1 transduced with irrelevant shRNA. To formally demonstrate the role of the inflammasome in P. acnes induced IL-1β processing and secretion, BMDC from mice were tested with targeted deletion of the inflammasome components ASC and NLRP3. Exposure of BMDC from ASC$^{-/-}$ and NLRP3$^{-/-}$ mice to P. acnes resulted in dramatically reduced levels of IL-1β secretion when compared to BMDC of wild-type mice (FIGS. 2f and 2g).

The NLRC4 inflammasome is not required for IL-1β release following exposure to *P. acnes* (FIG. 2h), likely due to the inability of *P. acnes* to form pores in the membrane of infected cells. Furthermore, using shRNA-transduced THP1 cells, it was observed that the NLR family member NLRP1 is also dispensable for IL-1β secretion upon exposure to *P. acnes* (FIG. 2d). These data demonstrate that *P. acnes* is a potent activator of the NLRP3 inflammasome resulting in processing and secretion of the mature form of IL-1β.

Example 3

Inflammasome Activation by *P. acnes* Requires ROS Production, $K^+$ Efflux, Phagocytosis and Induces Lysosomal Destabilization Bacteria were washed three times with PBS and then labeled with CFSE (1 mM) for 20 min at 37° C. and extensively washed with medium. THP1 cells or BMDC were infected with *P. acnes* for 6 h or 24 h, respectively. Subsequently, cells were extensively washed and analyzed by flow cytometry. Where indicated, Cytochalasin D (2.5 mM) was added to cells one hour before bacteria.

Figure 3:
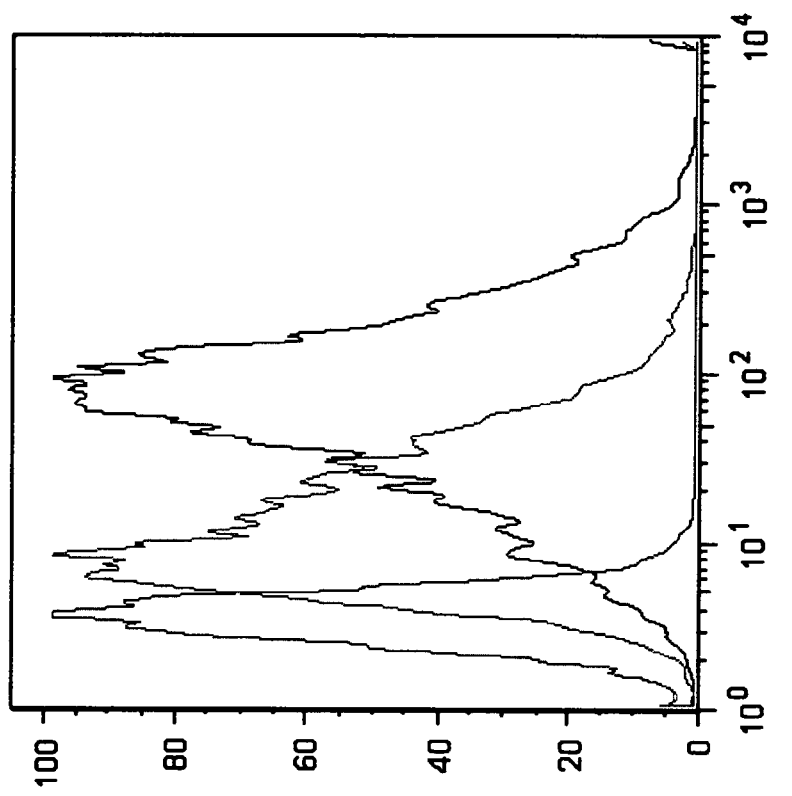
FIG. 3 shows cellular processes required for inflammasome activation.
Figure 3:
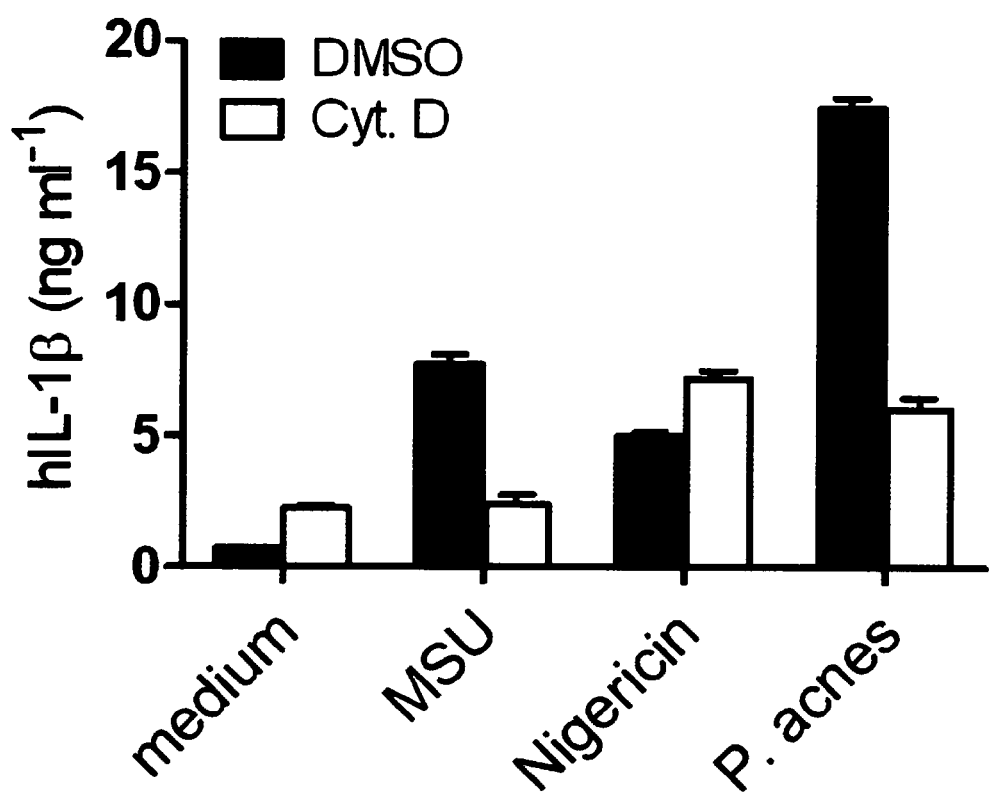
Figure 3:
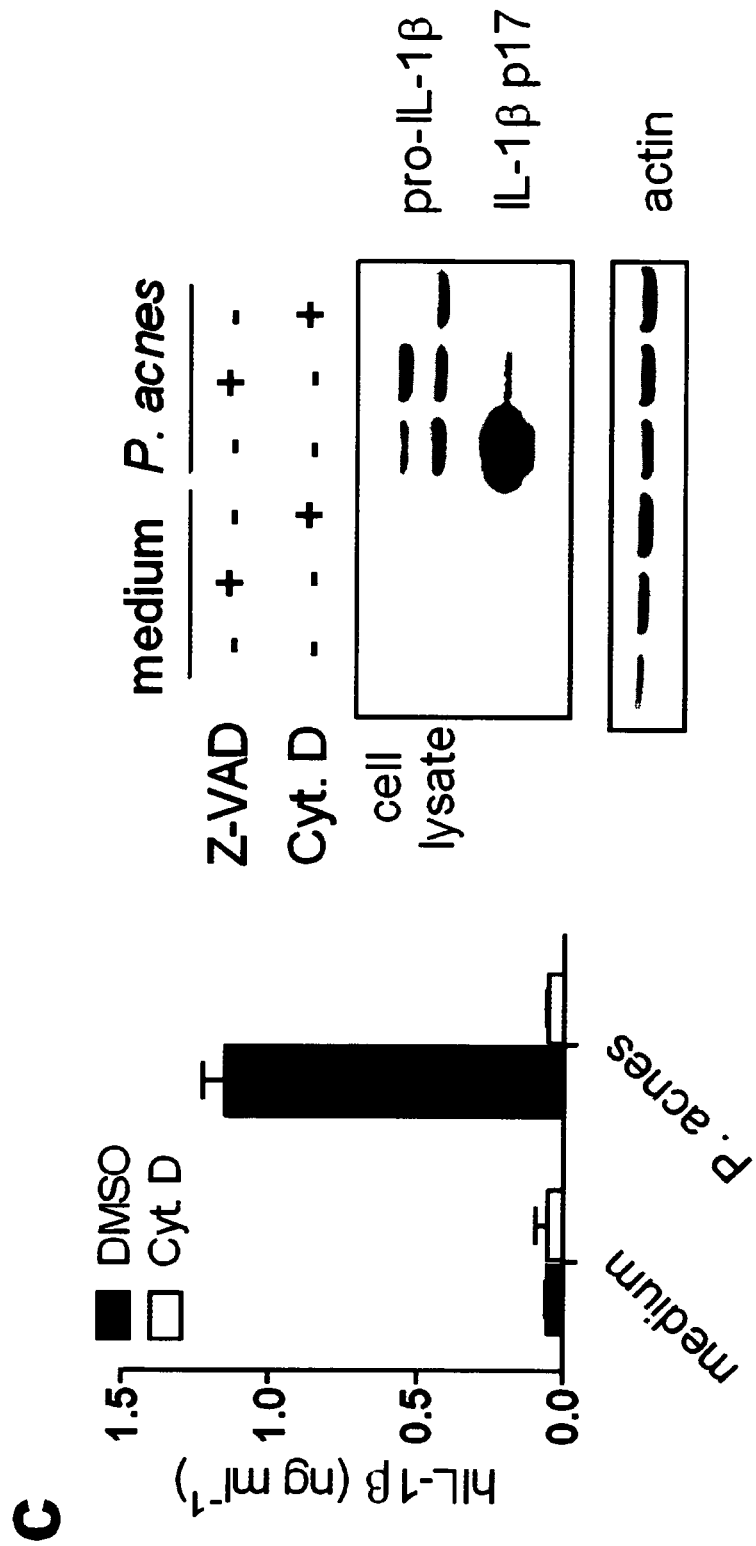
Figure 3:
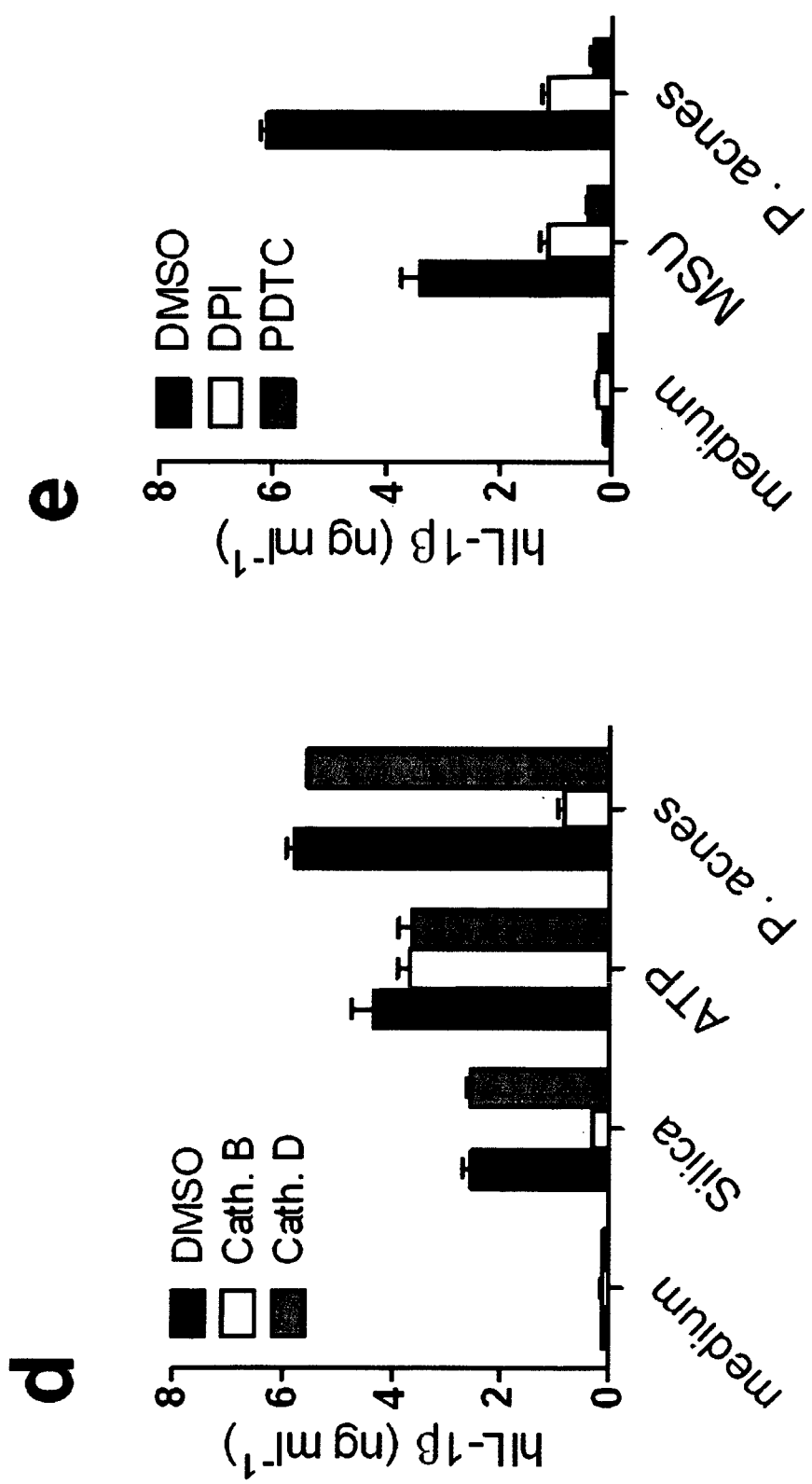
Figure 3:
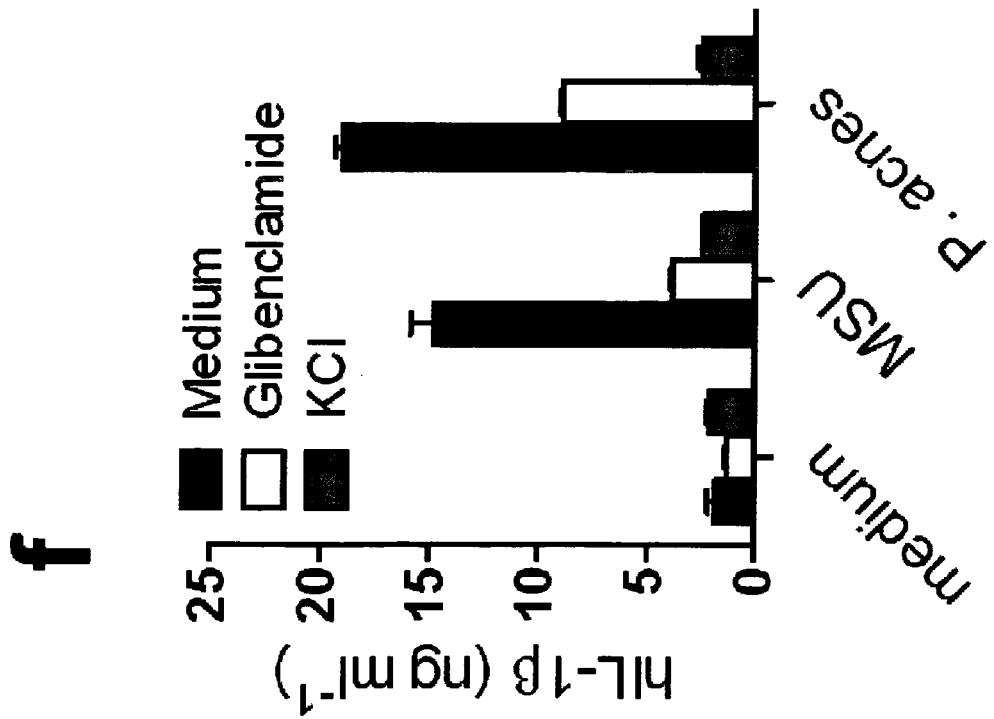
Figure 3:
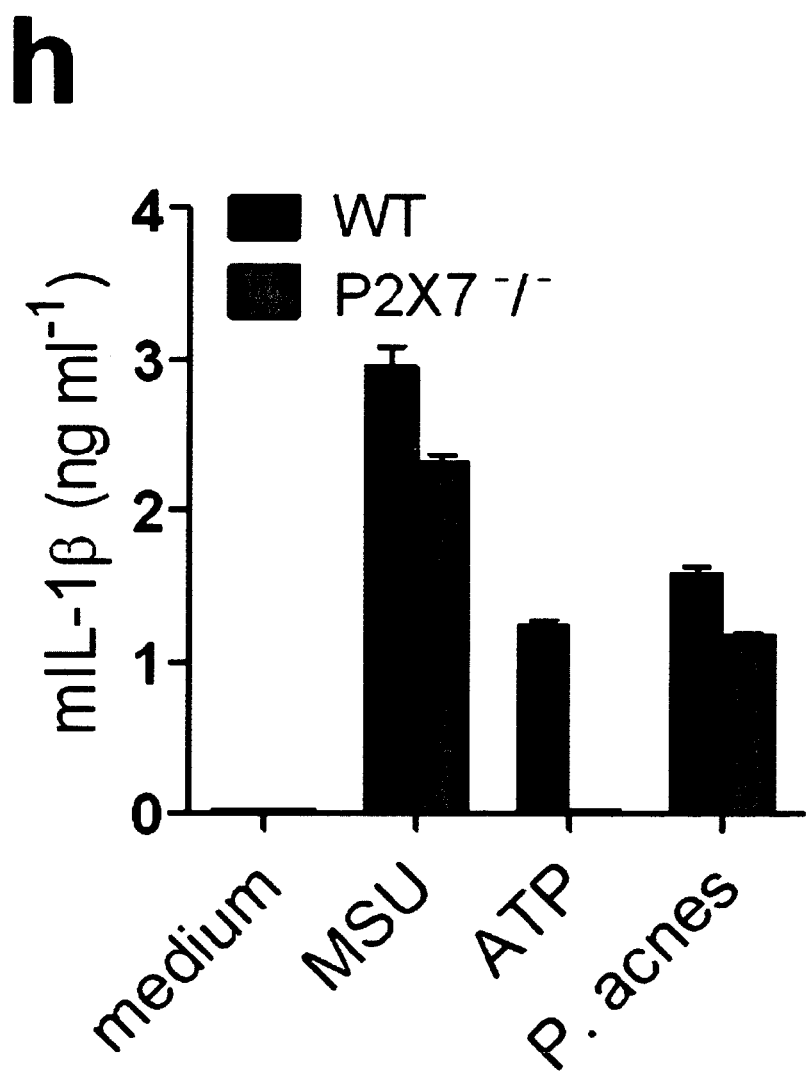

THP1 cells were treated with vehicle (DMSO) or cytochalasin D (Cyt. D, 2.5 mM) for one hour and then incubated with CFSE-labeled *P. acnes* (MOI=100) for 4 h or left untreated (FIG. 3a). Bacteria uptake was analyzed by FACS. Data are representative of one experiment repeated twice. FIG. 3b shows the IL-1β secretion from human monocytes primed with upLPS and treated with vehicle (DMSO) or cytochalasin D (Cyt.D, 2.5 mM). Non-upLPS-primed human monocytes were stimulated for 6 h with *P. acnes* in the absence (DMSO) or presence of cytochalasin D (Cyt. D, 2.5 mM) or Z-VAD-fmk (10 mM) (FIG. 3c). ELISA of secreted IL-1β (supernatant) and western blot of pro- and mature IL-1β p17 (cell lysates) are presented. FIG. 3d and e show the IL-1β secretion from human monocytes primed with upLPS and treated with cathepsin B—(Cath.B, 10 mM) or cathepsin D-inhibitor (Cath.D, 10 mM) (FIG. 3d) or ROS inhibitors (DPI, 10 mM; PDTC, 10 mM) (FIG. 3e). Potassium channel blockers (Glibenclamide, 100 mM; KCl, 65 mM) were added to upLPS-primed human monocytes one hour prior to stimulation with *P. acnes* (MOI=100), MSU (150 mg/ml), ATP (5 mM), silica (500 mg/ml) or nigericin (20 mM). IL-1β (FIG. 3f) and TNFα (FIG. 3g) release were determined after 6 h by ELISA. Secreted IL-1β from WT or P2X7$^{-/-}$ murine BMDC primed with upLPS and treated for 24 h with *P. acnes* (MOI=300) was measured by ELISA (FIG. 3h). Presented means and s.d are representative of at least three experiments.

Treatment of THP1 cells with Cyt. D abrogated the uptake of *P. acnes* (FIG. 3a). IL-1β maturation and secretion from upLPS-stimulated monocytes infected with *P. acnes* or stimulated with MSU was reduced by Cyt. D, whereas the response to the non-crystaline NLRP3 activator nigericin was not affected (FIG. 3b). Both pro-IL-1β synthesis and IL-1β release from non upLPS-stimulated human monocytes exposed to *P. acnes* were affected by Cyt D. (FIG. 3c). These observations demonstrate that the internalization process of the bacteria by APCs is essential for both NF-κB-dependent pro-IL1β synthesis (signal 1) and its cleavage into its active secreted form (signal 2). Furthermore, the specific blockage of Cathepsin B, but not Cathepsin D resulted in decreased IL-1β secretion form *P. acnes* infected- or silica stimulated-monocytes (FIG. 3d), showing that lysosomal rupture is needed in the IL-1β secretion process.

Human monocytes were pre-exposed to upLPS in order to generate pro-IL-1β and subsequently stimulated them with *P. acnes* in the presence of two ROS inhibitors, namely diphenyleneiodonium (DPI) a NADPH-oxidase inhibitor or PDTC. IL-1β secretion from cells exposed to *P. acnes* or MSU under these conditions was strikingly reduced in the presence of both ROS inhibitors (FIG. 3e). It has been previously shown that triggering of ROS in human granulocytes is caused by potassium efflux. Inhibiting K+ efflux, either by increased extracellular KCl concentration or by blockage of potassium channels with glibenclamide resulted in significant reduction of IL-1β release by *P. acnes* exposed- or MSU-stimulated cells (FIG. 3f) whereas TNF secretion was unaffected (FIG. 3g). It was also assessed whether cellular ATP release might play a role in *P. acnes*-induced IL-1β production. BMDC from ATP receptor P2X$_7$ deficient mice released similar amounts of IL-1β as cells from wild type mice when infected with *P. acnes* or stimulated with MSU while failing to respond to ATP (FIG. 3h).

Example 4

NLRP3 Inflammasome-Dependent In Vivo Inflammation is Independent of TLR2

C57BL/6 mice received three intraperitoneal (i.p.) injections of IL-1 receptor antagonist (IL-1Ra, Anakinra, 150 mg/kg) or PBS at 8 h intervals. One hour after first i.p. injection of IL-1Ra mice received intradermal injections of *P. acnes* or PBS. TNFα inhibitor (Etanercept) and anti-IL-1β antibody treated mice (Canakinumab, 200 mg/mouse) C57BL/6 mice received i.p. injection 24 h before an intradermal injection of *P. acnes* or PBS. To make bone marrow chimeras indicated mice were lethally irradiated (10 Gy) and subsequently transplanted with indicated bone marrow. After bone marrow reconstitution (8 weeks later) mice were interdermally injected with *P. acnes* or PBS.

The ear thickness was measured using a micro caliper before and 24 h after bacterial injection. The percentage of ear thickness was calculated by comparing the ear thickness before and 24 hours after injection.

Figure 4:
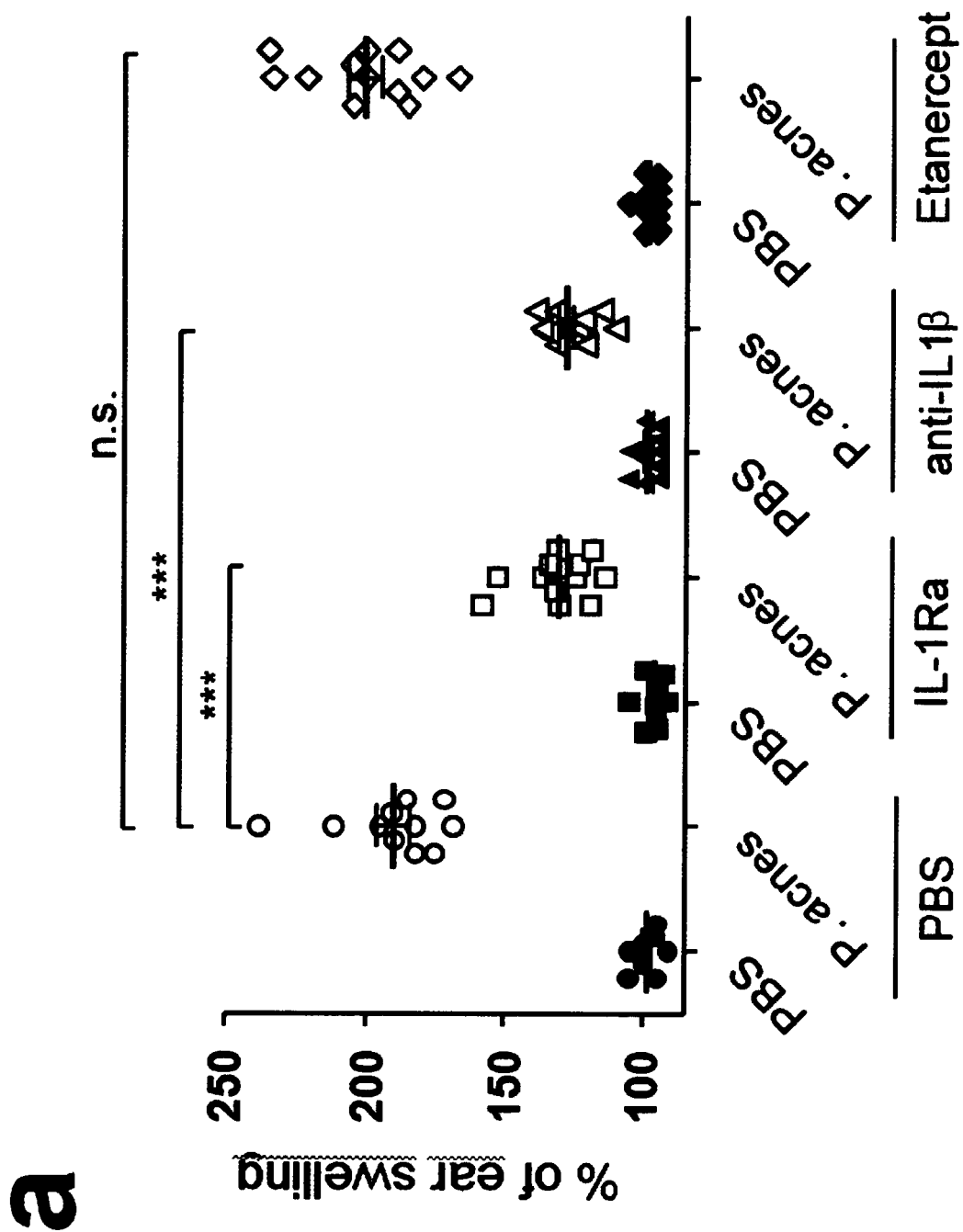
FIG. 4 shows the influence of TLR2 on NLRP3 inflammasome-dependent in-vivo-inflammation.
Figure 4:
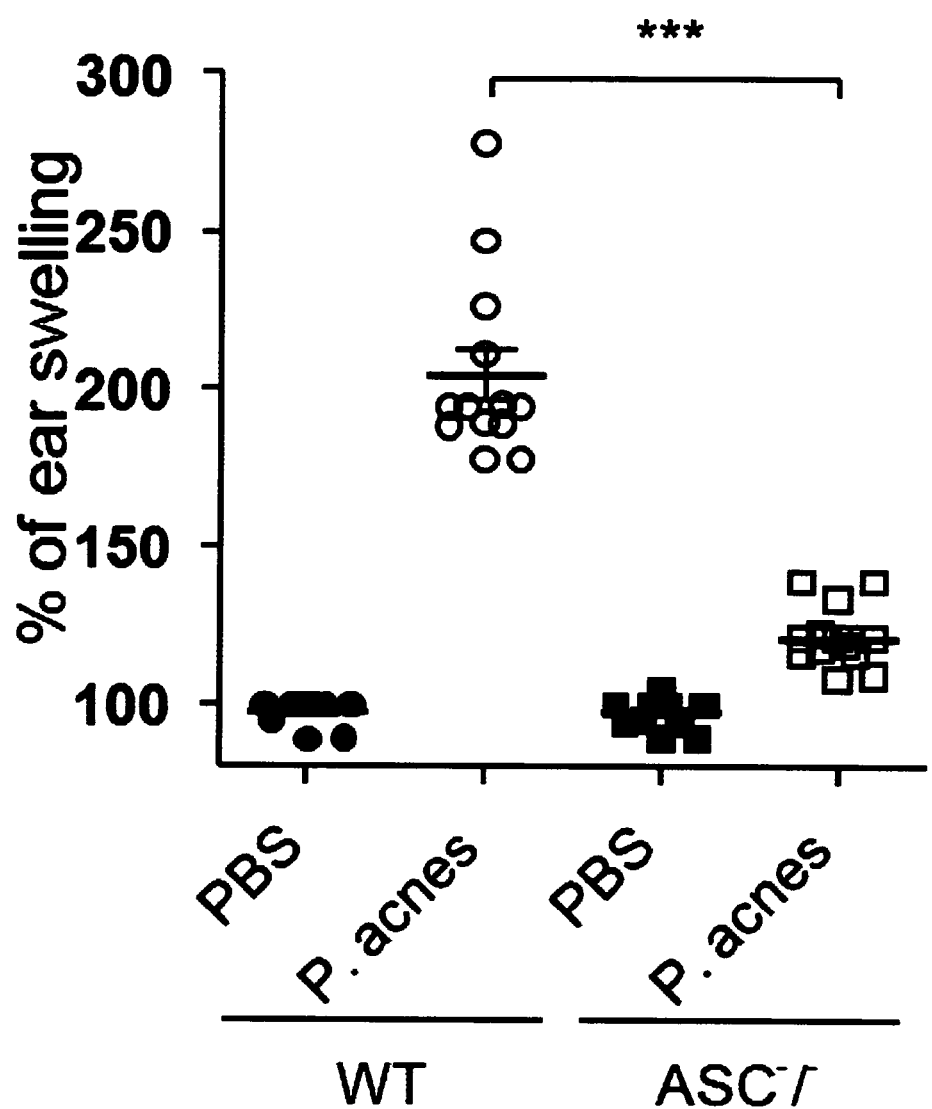
Figure 4:
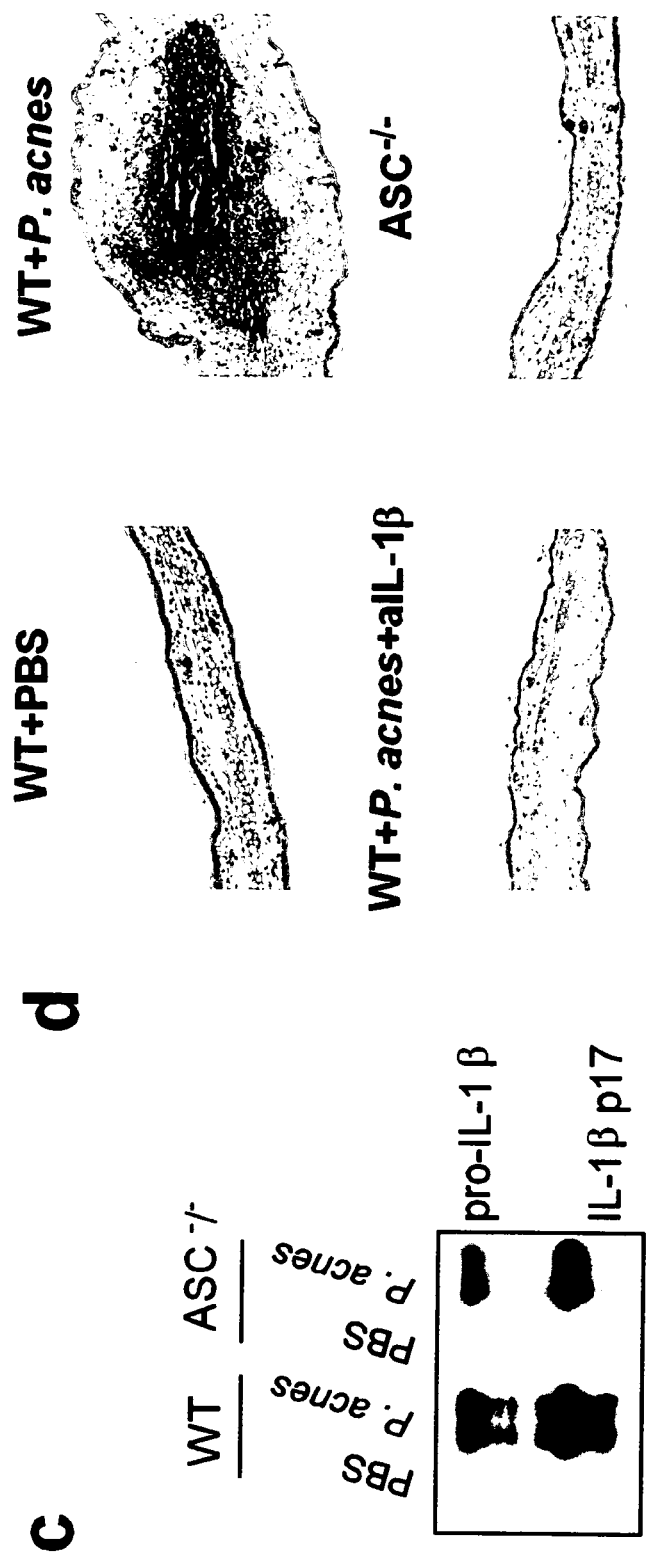
Figure 4:
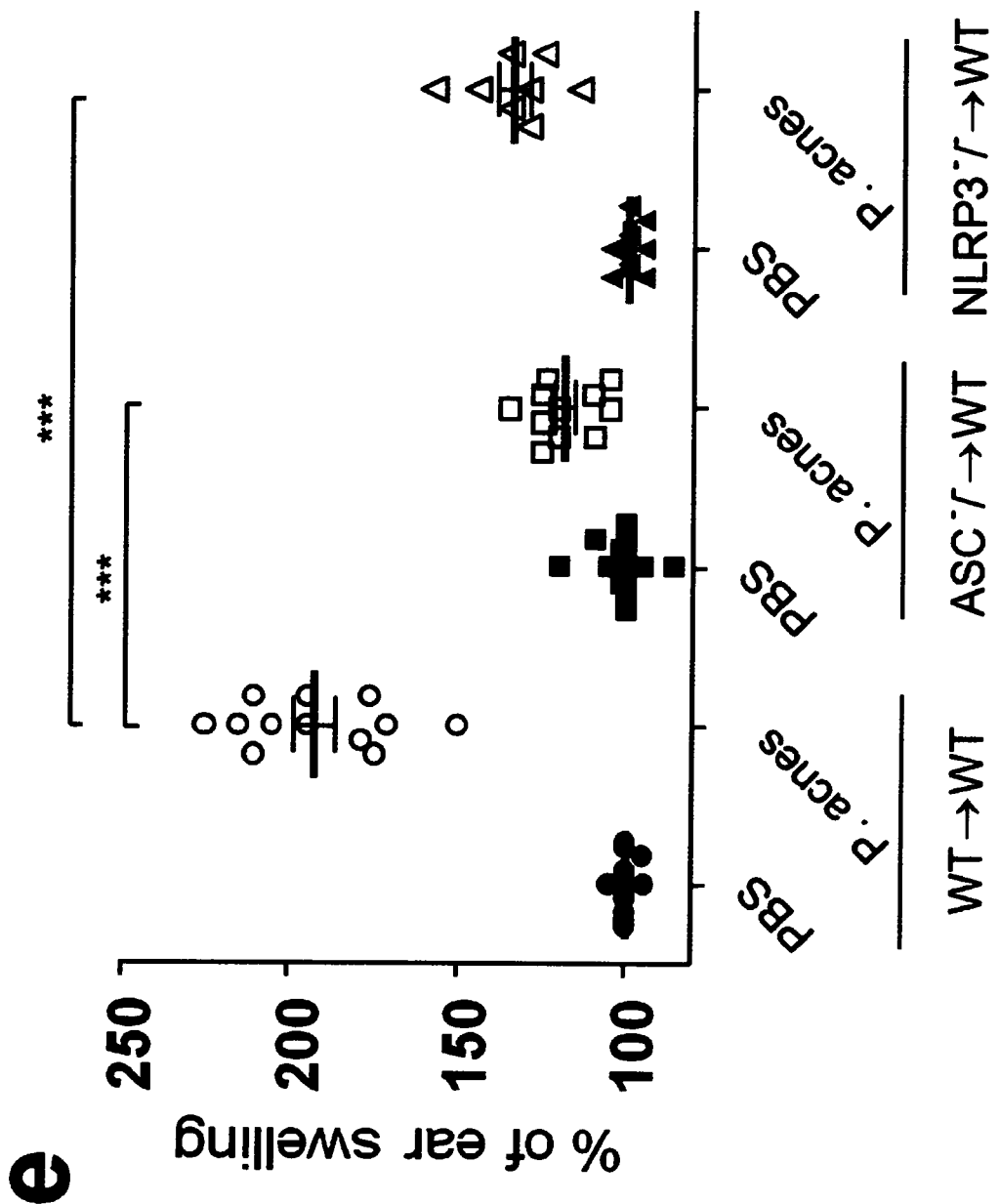
Figure 4:
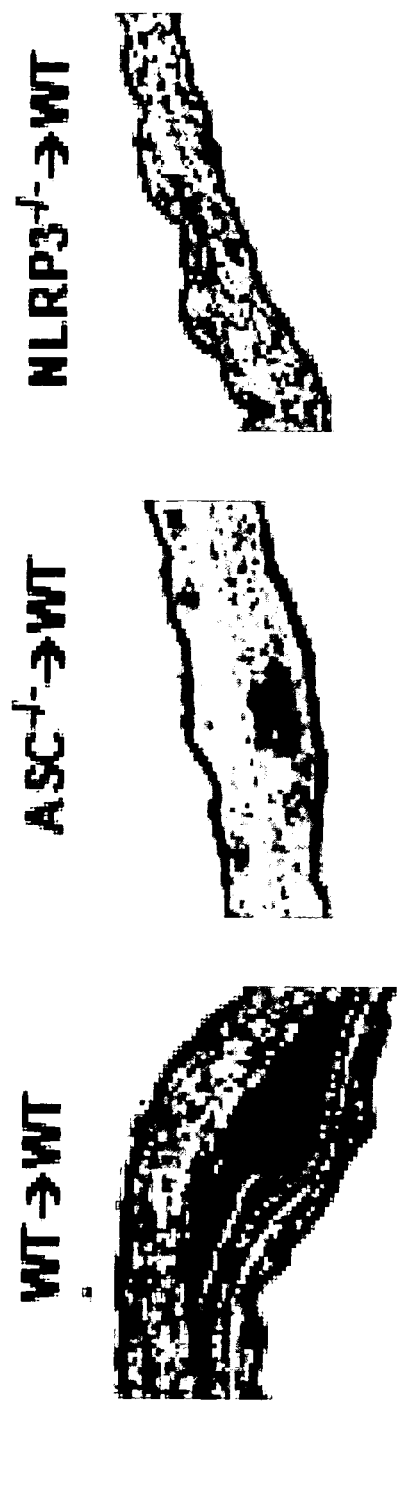
Figure 4:
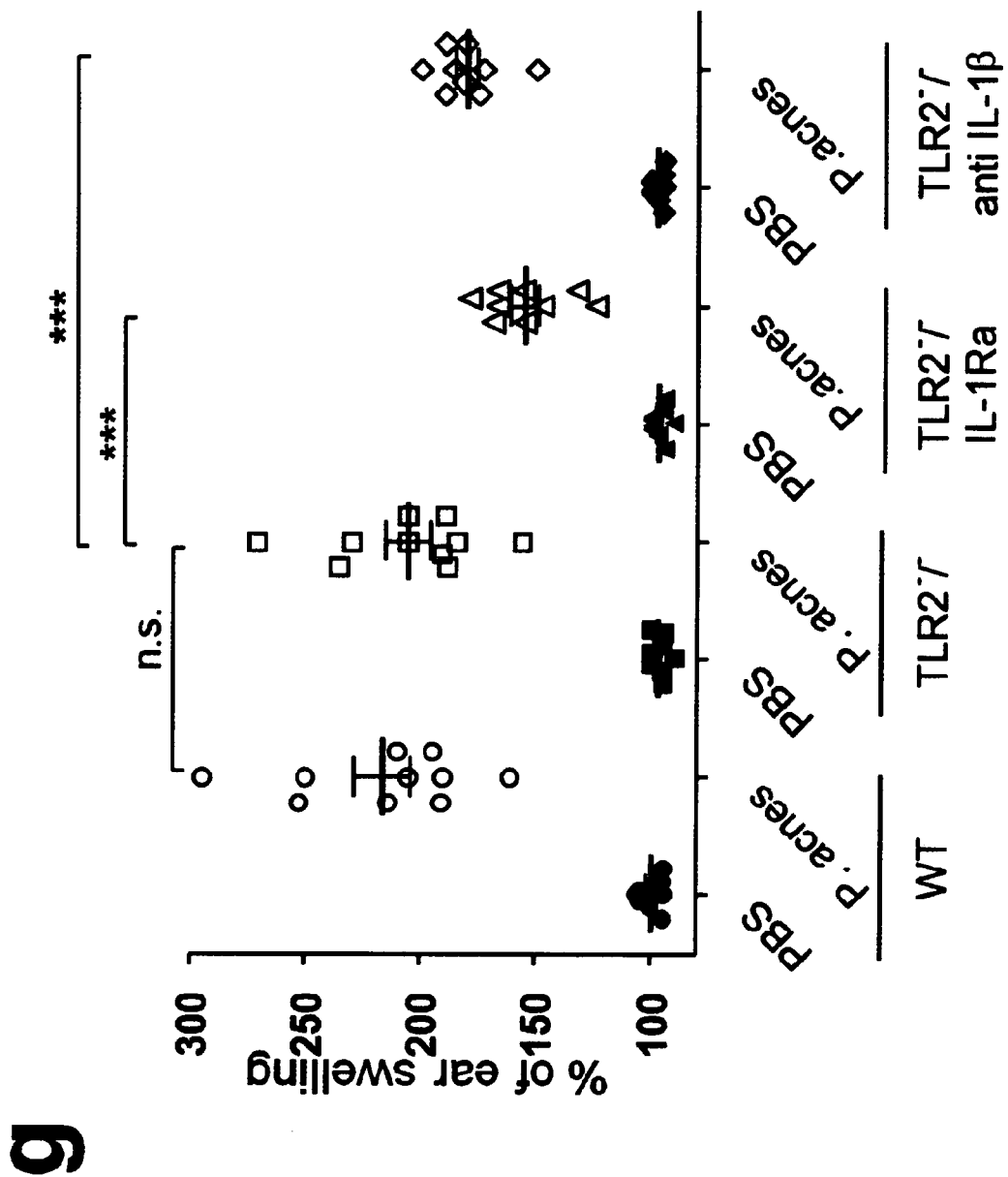
Figure 4:
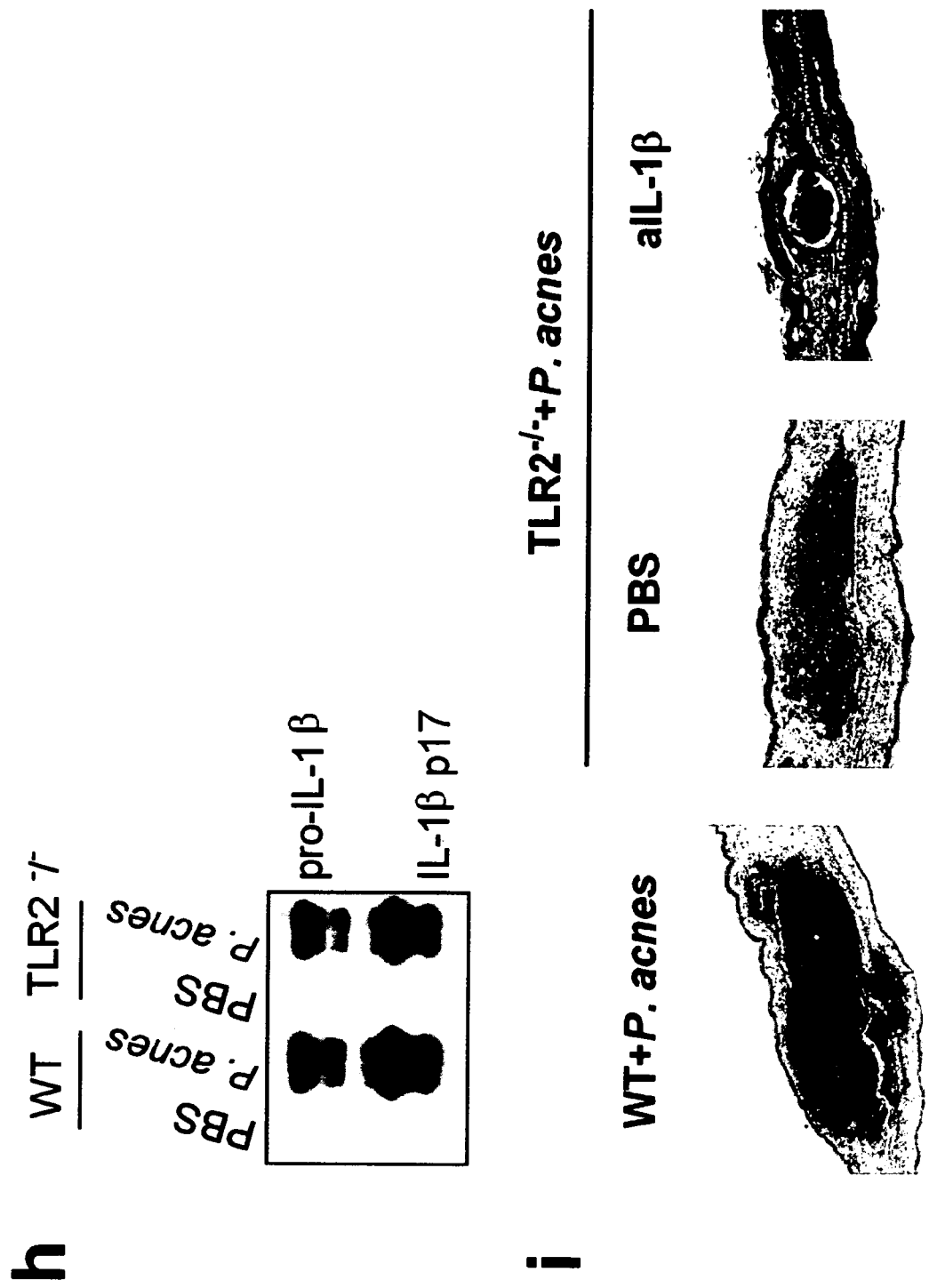

WT mice were injected intradermally with *P. acnes* (20× $10^6$ CFU/20 ml in PBS, left ear) or with an equal amount of PBS (right ear) (FIG. 4a). Mice were treated with vehicle (n=11) or three intraperitoneal injections of IL-1Ra (Anakinra, 150 mg/kg, n=13) at the 8 h intervals or a single i.p. injection of anti-IL1β antibody (200 mg/ml) one hour prior to *P. acnes* or PBS challenge. The ear swelling as measured 24 hrs later is presented. ASC$^{-/-}$ mice were challenged the same way with *P. acnes*. The resulting ear swelling (FIG. 4b) and pro- and mature-IL1β in ear extracts (FIG. 4c) are presented. FIG. 4d shows the Histology (HE) of WT mice having received *P. acnes* plus PBS, Anakinra or anti-IL1β treatment. Histology of an ASC$^{-/-}$ mouse challenged with *P. acnes* is also shown in FIGS. 4e and f. WT mice reconstituted with WT (n=8-10), ASC$^{-/-}$ (n=12) or NLRP3$^{-/-}$ (n=8) bone marrow were challenged with *P. acnes* or PBS as described above. The resulting swelling (FIG. 4e) and histology of the infected ear (FIG. 4f) are presented. TLR2$^{-/-}$ (n=10) were intradermally injected with *P. acnes* or PBS one hour after treatment with IL-1Ra (n=10) or anti-IL-1β antibody (n=9) as described above. The resulting ear swelling (FIG. 4g) and histology (FIG. 4i) are presented. Western blot analysis of pro- and mature IL-1β did not show any difference between WT and TLR2$^{-/-}$ mice (FIG. 4h).

Injection of 20×$10^6$ CFU *P. acnes* intradermally in the ear of C57BL/6 WT mice resulted in manifest ear swelling (FIG.

4a), production of pro- and mature IL-1β (FIG. 4c) and abundant subcutaneous neutrophil infiltration resembling a pustule at the site of P. acnes injection all within 24 h (FIG. 4d). When C57BL/6 WT mice were compared to ASC-deficient mice, ear swelling (FIG. 4b), production of pro- and mature IL-1β (FIG. 4c) and subcutaneous neutrophil infiltration (FIG. 4d) were all dramatically reduced. In NLRP3$^{-/-}$ mice the above features were similarly to ASC$^{-/-}$ mice strongly reduced.

P. acnes-infected mice were treated intraperitoneally prior to intradermal P. acnes injection with IL-1 receptor antagonist (IL-1Ra) or anti-IL-1β antibody. In this case also, a significant reduction in ear swelling (FIG. 4a) and subcutaneous neutrophil infiltration was observed in IL-1Ra and anti-IL1β-treated (FIG. 4d), confirming the crucial role of in situ IL-1β production for P. acnes induced neutrophil infiltration of the skin.

A bone marrow transplantation was performed after lethal irradiation in order to generate WT mice reconstituted with WT, ASC$^{-/-}$ or NLRP3$^{-/-}$ myeloid cells. After verification of chimerism in the ASC$^{-/-}$ or NLRP3$^{-/-}$ bone marrow transplanted mice, chimeras were injected intradermally with P. acnes as above. Ear swelling (FIG. 4e) and neutrophilic infiltration of the skin (FIG. 4f) was dramatically reduced in chimeric mice harboring ASC$^{-/-}$ or NLRP3$^{-/-}$ myeloid cells when compared mice transplanted with WT bone marrow, indicating that myeloid and radiosensitive cells, but stromal cells such as keratinocytes or sebocytes mediate the cutaneous inflammatory responses to P. acnes.

To determine if TLR2 signaling is required for the inflammatory skin response to P. acnes in vivo, P. acnes was injected intradermally to TLR2-deficient mice and compared ear swelling and inflammatory infiltration of the injected ear to that of wild-type mice and ASC$^{-/-}$ mice. No significant difference in ear swelling or cutaneous inflammation was observed between TLR2$^{-/-}$ and wild-type mice (FIG. 4g). Moreover, production of pro-IL-1β as detected by western blotting of infected ears (FIG. 4h), did not require TLR2, as IL-1β levels were similar in the ears of TLR2-deficient and wild-type mice. Furthermore, treatment of TLR2$^{-/-}$ mice with IL1-RA or anti-IL-βantibody blocked the development of ear swelling (FIG. 4g) and cutaneous inflammation (FIG. 4i), formally demonstrating that the cutaneous inflammatory response observed in the ears of P. acnes infected mice dependent on IL-1β production and independent of TLR2 signaling.

The invention claimed is:

1. A method for the treatment of acne, comprising administering an effective amount of an inhibitor capable of binding to IL-1β, with a dissociation constant of at most $10^{-8}$ mol/l, wherein the inhibitor is selected from an IL-1β antibody, and an antibody fragment.

2. The method according to claim 1, wherein the inhibitor is selected from the group consisting of canakinumab and gevokizumab and LY21899102.

* * * * *